United States Patent
Takagi et al.

(10) Patent No.: US 6,752,777 B1
(45) Date of Patent: Jun. 22, 2004

(54) BLOOD COMPONENT COLLECTING APPARATUS

(75) Inventors: Yoshiki Takagi, Fujinomiya (JP); Atsushi Suzuki, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/412,571

(22) Filed: Oct. 5, 1999

Related U.S. Application Data

(63) Continuation-in-part of application No. 09/094,593, filed on Jun. 15, 1998, now abandoned.

(30) Foreign Application Priority Data

Jun. 16, 1997 (JP) .............................................. 9-176499
Oct. 5, 1998 (JP) ........................................... 10-299135

(51) Int. Cl.[7] .......................... A61M 37/00; C02F 1/38; B04B 9/10; B01D 43/00
(52) U.S. Cl. .................... 604/6.01; 604/4.01; 604/6.07; 210/782; 494/7; 494/37
(58) Field of Search ....................... 422/44–8; 604/4.01, 604/5.01, 6.01–6.07, 6.09, 6.1, 6.11, 6.15, 6.16; 210/645, 650, 767, 781–782, 784, 85, 87–90, 252, 256, 257.1–257.2, 258–9, 282; 494/37, 43, 7, 56, 60

(56) References Cited

U.S. PATENT DOCUMENTS

| | | | |
|---|---|---|---|
| 4,049,192 A | | 9/1977 | Krebs et al. |
| 4,416,654 A | * | 11/1983 | Schoendorfer et al. ....... 494/10 |
| 4,464,167 A | | 8/1984 | Schoendorfer et al. |
| 4,776,964 A | | 10/1988 | Schoendorfer et al. |
| 5,273,517 A | * | 12/1993 | Barone et al. ................. 251/5 |
| 5,348,533 A | * | 9/1994 | Papillon et al. ............ 604/6.07 |
| 5,437,624 A | * | 8/1995 | Langley ..................... 604/6.05 |
| 5,514,070 A | | 5/1996 | Pages |

FOREIGN PATENT DOCUMENTS

| | | | |
|---|---|---|---|
| EP | 0 885 619 | | 12/1998 |
| JP | 5-326117 | | 12/1993 |
| JP | 7-308375 | | 11/1995 |
| JP | 7-313588 | | 12/1995 |
| JP | 08117331 A | * | 5/1996 |
| JP | 08117331 | * | 5/1996 |
| JP | 8-131539 | | 5/1996 |
| JP | 8-136537 | | 5/1996 |
| JP | 8-177330 | | 5/1996 |
| WO | WO94/25086 | | 11/1994 |
| WO | WO96/40399 | | 12/1996 |

* cited by examiner

*Primary Examiner*—Patricia M. Bianco
(74) *Attorney, Agent, or Firm*—Burns, Doane, Swecker & Mathis, LLP

(57) ABSTRACT

Platelets are collected from blood by delivering blood from a blood source to a centrifugal separator and operating the separator to separate plasma from the blood. The separated plasma is collected in a plasma collecting bag. After a predetermined amount of plasma has been collected in the bag, the plasma is circulated between the bag and the separator. That procedure is repeated at least once to build-up the amount of collected blood. Then platelets are collected by delivering additional blood to the separator and circulating plasma between the separator and the plasma collecting bag at an accelerating circulation rate while rotating the rotor to remove platelets from the separator. The platelets are collected in a platelet collecting bag. Then, blood remaining in the separator is returned to the blood source.

4 Claims, 16 Drawing Sheets

BLOOD COMPONENT COLLECTING APPARATUS

This application is a continuation in part of U.S. patent application Ser. No. 09/094,593 filed Jun. 15, 1998 now abandoned.

BACKGROUND OF THE INVENTION

The present invention relates to a blood component collecting apparatus and a blood component collecting circuit for separating predetermined blood components from the blood.

For effectively utilizing the blood and reducing the burden on the blood donor in the blood-collection, the collected blood is separated into various blood components centrifugally to extract only the components required for the donee, and the remaining components are returned to the donor.

In the case where a platelet product is produced from this blood component collection process, the blood donated from the donor is introduced to a blood component collecting circuit, separated into four components of plasma, white cells, platelets and red cells by a centrifugal separator called the centrifugal bowl installed in the blood component collecting circuit. Among these blood components, the platelets are recovered in a container to produce a platelet product. Meanwhile the remaining components including the plasma, white cells and red cells are returned to the donor.

Methods of collecting the platelets, first and second methods, are disclosed in WO 94/25086. In the first method, a liquid is sent to the centrifugal bowl and added to the whole blood while being diluted at a predetermined flow rate. According to the second method, the whole blood is sent to the centrifugal bowl and centrifugally separated into a low-density component, a middle-density component and a high-density component. The low-density component is retrieved in a first container, and the circuit is switched to circulate the low-density component at a first flow rate (fixed rate) to expand the middle-density component area in the centrifugal bowl, and the middle-density component, while being recirculated at a second flow rate (acceleration), is retrieved.

The first method, however, requires three pumps including an ACD pump, a blood collecting-returning pump and a circulation pump, and thus enlarges the apparatus size. In the second method, on the other hand, the platelets can be collected by two pumps, thus reducing the apparatus size. Nevertheless, the collected platelets are likely to be mixed with white cells, which fails to meet the requirement of the liquid containing platelets for a platelet product demanded to contain as few white cells as possible.

Accordingly, the object of the present invention is to provide a compact blood component collecting apparatus and a blood component collecting circuit used therein which is capable of producing a high-concentration platelets-contained liquid with low content of white cells at a high platelet collecting efficiency.

SUMMARY OF THE INVENTION

The aforementioned object of the invention can be achieved by a blood component collecting apparatus which comprises a blood component collecting circuit including: a centrifugal separator having a rotor having an internal blood storage space, an inlet and an outlet communicating with said blood storage space for centrifugally separating the blood introduced therein through said inlet by rotation of said rotor; a first line for connection between a blood-collection needle or a blood-collection unit connector and said inlet of said centrifugal separator; a second line connected to said outlet of said centrifugal separator; a third line connected to said first line for injecting an anticoagulant; a plasma collecting bag having a first tube connected to a middle point of said first line and a second tube connected to said second line; and a platelet collecting bag connected to said second line; said blood component collecting apparatus further comprising a centrifugal separator drive unit for rotating said rotor of said centrifugal separator, a first liquid supply pump for said first line arranged at a position of said first line between said centrifugal separator and a connecting portion for connecting said first tube to said first line, a second liquid supply pump for said third line, a plurality of flow path shutter means for opening/closing the flow paths of said blood component collecting circuit; and a controller for controlling said centrifugal separator drive unit, said first liquid supply pump, said second liquid supply pump and said plurality of flow path shutter means; wherein said controller controls said centrifugal separator drive unit, said first liquid supply pump, said second liquid supply pump and said plurality of flow path shutter means so as to execute a platelet collecting operation which includes at least twice of plasma collecting-circulation steps including a plasma collecting step for collecting blood added anticoagulant by starting said first and second liquid supply pumps and collecting said plasma obtained from said blood in said plasma collecting bag by activating said centrifugal separator drive unit and a plasma circulation step for temporarily suspending blood-collection subsequent to said plasma collecting step and circulating said plasma contained in said plasma collecting bag to said centrifugal separator by activating said centrifugal separator drive unit, subsequent to said plasma collecting-circulation steps, a platelet collecting step for collecting platelet released from said centrifugal separator into said platelet collecting bag by accelerating a plasma circulation rate by said first liquid supply pump; and to execute a blood returning step, subsequent to said platelet collecting step, for returning said blood contained in said centrifugal separator.

Further, the aforementioned object of the invention can be achieved by a blood component collecting circuit which comprises a centrifugal separator having an inlet and an outlet; a blood-collection needle or a blood-collection unit connector; a first line having a first pump tube for connection between said blood-collection needle or said blood-collection unit connector and the inlet of said centrifugal separator; a second line connected to the outlet of said centrifugal separator; a third line having a second pump tube connected to a portion near said blood-collection needle or said blood-collection unit connector of said first line; a plasma collecting bag having a first tube connected to a portion of said first line between said blood-collection needle or said blood-collection unit connector and said first pump tube and a second tube connected to said second line; a platelet collecting bag having a third tube connected to said second line; and a cassette housing for partially containing and partially holding said first line, said second line, said third line, said first tube, said second tube and said third tube; wherein said first pump tube and said second pump tube are fixed on said cassette housing so as to extend therefrom; wherein said cassette housing includes a first opening for exposing the portion of said first line between said blood-collection needle or said blood-collection unit connector and said first pump tube and capable of being intruded by a flow path shutter means, a second opening for exposing said first pump tube and capable of being intruded by a flow path shutter means, a third opening for exposing said second tube and capable of being intruded by a flow path shutter means, a fourth opening for exposing said third tube and capable of being intruded by a flow path shutter means, a fifth opening for exposing the portion of said second line between said centrifugal separator and a connecting portion for connecting said fourth tube to said second line and capable of being intruded by a flow path shutter means.

Further, the aforementioned object of the invention can be achieved by a blood component collection apparatus comprising a blood component collection circuit including: a centrifugal separator having a rotor, an internal blood storage space, an inlet and an outlet communicating with said blood storage space and centrifugally separating blood introduced thereinto through said inlet by a rotation of said rotor; a first line for connecting a connecting portion of a blood collection needle or a blood collection instrument and said inlet of said centrifugal separator with each other; a second line connected to said outlet of said centrifugal separator; a third line connected to said first line, for injecting an anticoagulant to said blood; a plasma collection bag having a first tube connected with said first line and a second tube connected with said second line; and a platelet collection bag connected with said second line; said blood component collection apparatus further comprising: a centrifugal separator drive unit for rotating said rotor of said centrifugal separator; a first liquid supply pump which is used for said first line and located at a position of said first line between said centrifugal separator and a connecting portion for connecting said first tube to said first line; a second liquid supply pump which is used for said third line; a plurality of flow path shutter means for opening/closing flow paths of said blood component collection circuit; and a controller for controlling said centrifugal separator drive unit, said first liquid supply pump, said second liquid supply pump, and a plurality of said flow path shutter means; wherein said controller controls said centrifugal separator drive unit, said first liquid supply pump, said second liquid supply pump, and a plurality of said flow path shutter means to execute a platelet collection operation including: a plasma collection/constant-speed circulation step including a first plasma collection step of collecting anticoagulant-added blood by starting said first and second liquid supply pumps and collecting a predetermined amount of plasma into said plasma collection bag by activating said centrifugal separator drive unit; and a constant-speed plasma circulation step which is executed after said execution of said first plasma collection step terminates to temporarily suspend a blood collection and circulate said plasma contained in said plasma collection bag to said centrifugal separator at a constant speed by activating said centrifugal separator drive unit; a plasma collection/acceleration circulation step including a second plasma collection step which is executed after said execution of said plasma collection/constant-speed circulation step terminates to collect said anticoagulant-added blood by starting said first and second liquid supply pumps and collect said plasma by activating said centrifugal separator drive unit; and an acceleration plasma circulation step which is executed after said execution of said second plasma collection step is executed to temporarily suspend said blood collection and circulate said plasma contained in said plasma collection bag to said centrifugal separator at an accelerated speed by activating said centrifugal separator drive unit, a platelet collection step which is executed after said execution of said plasma collection/acceleration circulation step terminates to flow out platelets from said centrifugal separator and collect said platelets into said platelet collection bag by accelerating a plasma circulation rate by means of said first liquid supply pump, and a blood return step which is executed after said execution of said platelet collection step terminates to return said blood inside said centrifugal separator to a donor.

DETAILED DESCRIPTION OF THE PREFERRED EMBODIMENTS

Figure 1:
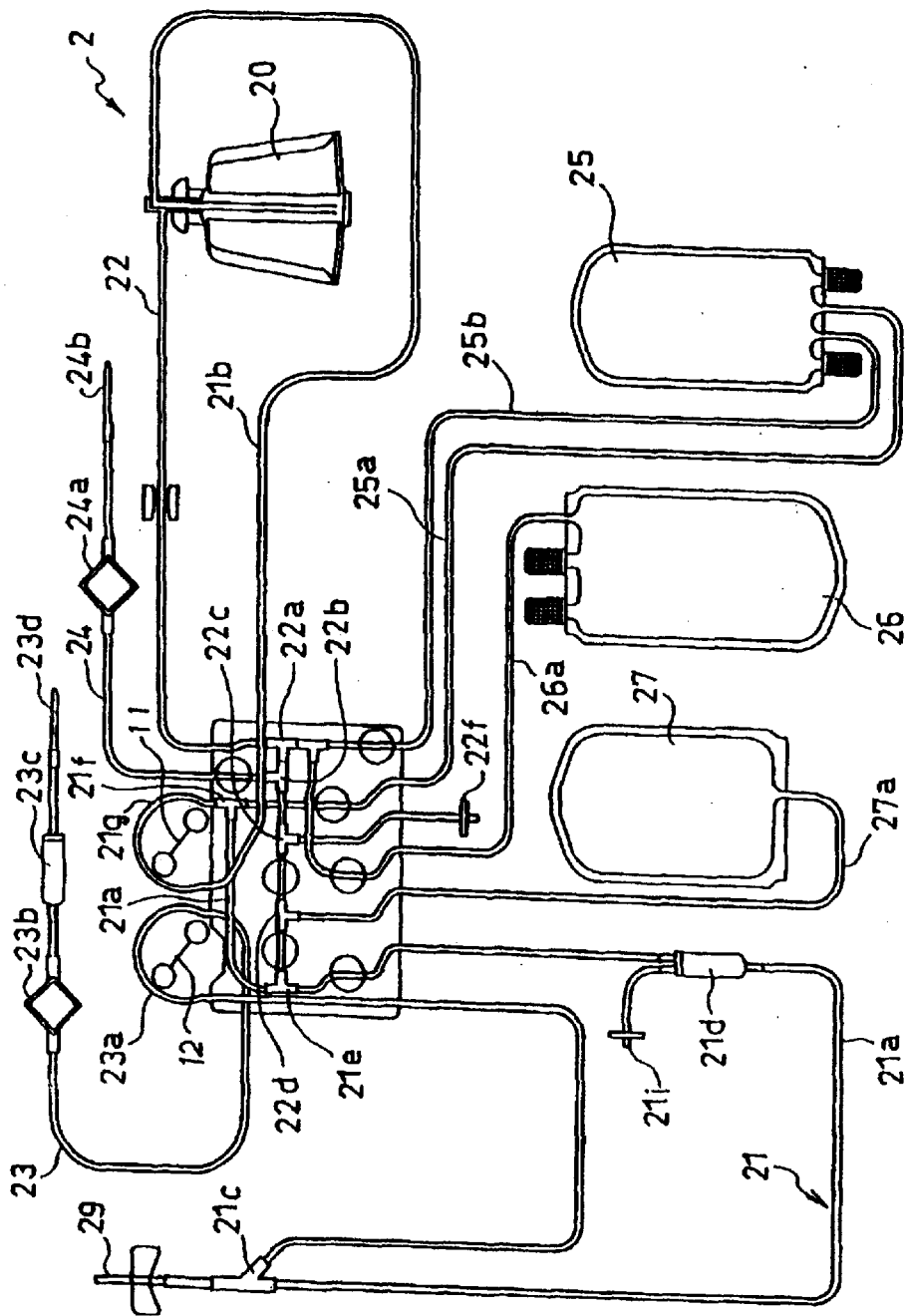
FIG. 1 is a schematic drawing of an example configuration of a blood component collecting circuit used in a blood component collecting apparatus according to the present invention.

A blood component collecting apparatus according to the present invention will be described with reference to an embodiment shown in the accompanying drawings.

A blood component collecting apparatus 1 according to the invention is provided with a blood component collecting circuit 2 including a centrifugal separator 20 having a rotor 142 having an internal blood storage space, an inlet and an outlet communicating with the blood storage space for centrifugally separating, in the blood storage space, the blood introduced therein through the inlet by the rotation of the rotor 142, a first line 21 for connection between a connector of a blood-collection needle 29 or a blood pool and the inlet of the centrifugal separator 20, a second line 22 connected to the outlet of the centrifugal separator 20, a third line 23 connected to the first line 21 for injecting an anticoagulant, a plasma collecting bag 25 having a first tube 25a connected to the first line 21 and a second tube 25b connected to the second line 22, and a platelet collecting bag 26 connected to the second line 22.

The blood component collecting apparatus 1 has a centrifugal separator drive unit 10 for rotating the rotor 142 of the centrifugal separator 20, a first liquid supply pump 11 for the first line 21, a second liquid supply pump 12 for the third line 23, a plurality of flow path shutter means 81, 82, 83, 84, 85, 86, 87 for opening/closing the flow paths of the blood component collecting circuit 2, and a controller 13 for controlling the centrifugal separator drive unit 10, the first liquid supply pump 11, the second liquid supply pump 12 and a plurality of the flow path shutter means 81, 82, 83, 84, 85, 86, 87.

First, the blood component collecting circuit 2 will be explained.

The blood component collecting circuit 2 is used for collecting the blood components, more specifically, the platelets. The blood component collecting circuit 2 is provided with a blood collector such as a blood-collection needle 29 or a connector (blood collector connector) for connecting a blood collector such as a blood-collection needle 29 or a blood pool connector, a first line 21 (blood-collection/returning line) having a first pump tube 21g for connection between the blood-collection needle 29 or the blood collector connector and the inlet of the centrifugal separator 20, a second line 22 for connection between the outlet of the centrifugal separator 20 and the first line 21, a third line (anticoagulant injection line) 23 having a second pump tube 23a connected to a portion of the first line 21 near the blood-collection needle 29 or the blood collector connector, a plasma collecting bag 25 having a first tube 25a connected to the portion of the first line 21 between the blood-collection needle 29 or the blood collector connector and the pump tube 21g and a second tube 25b connected to the second line 22, a platelet collecting bag 26 having a third tube 26a connected to the second line 22, a buffy coat collecting bag 27 having a fourth tube 27a connected to the second line 22, and a fourth line 24 for injecting liquid (physiological salt solution) connected to the second line 22. The blood component collecting circuit 2 may employ a connector (such as a metal or plastic needle) for connecting a blood pool such as a blood bag rather than the blood-collection needle.

The first liquid supply pump 11 for said first line is arranged at a position ( first pump tube 21g) of the first line between said centrifugal separator and a connecting portion for connecting the first tube to said first line. The second liquid supply pump 12 for said third line is arranged at second pump tube 23a.

Conventionally a known metal needle is used as the blood-collection needle 29. The first line 21 includes a portion 21a to which the blood-collection needle 29 is connected and a portion 21b to which the inlet of the centrifugal separator 20 is connected. The first line portion 21a closer to the blood-collection needle is formed by a plurality of soft plastic tubes connected thereto. The portion 21a of the first line 21 closer to the blood-collection needle has such elements arranged as viewed from the blood-collection needle side, a branching connector 21c for connecting the third line 23, a chamber 21d for removing bubbles and micro-aggregates, a branching connector 21e for connecting the second line 22, and a branching connector 21f for connecting the first tube 25a communicated with the plasma collecting bag 25. The chamber 21d is connected to an air-permeable, germ-blocking filter 21i. The first line portion 21b closer to the centrifugal separator 20 is connected to a branching connector 21f for connecting the first tube 25a and has a pump tube 21g formed in the vicinity thereof.

The second line 22 for connection between the outlet of the centrifugal separator 20 and the first line 21 has an end thereof connected to the outlet of the centrifugal separator 20 and the other end thereof connected to the branching connector 21e for connecting the first line 21. The second line 22 has such elements arranged as viewed from the centrifugal separator side, a branching connector 22a for connecting the second tube 25b communicated with the plasma collecting bag 25 and the third tube 26a communicated with the platelet collecting bag 26, a branching connector 22b for connecting the fourth line 24, a branching connector 22c for connecting a tube having a bubble-removing filter 22f, and a branching connector 22d for connecting the fourth tube 27a communicated with the buffy coat collecting bag 27.

The third line 23 is connected to the branching connector 21c having an end thereof connected to the first line 21. The third line 23 has such elements as a pump tube 23a, a foreign matter removing filter 23b, a bubble removing chamber 23c and an anticoagulant container connecting needle 23d arranged as viewed from the connector 21c.

One end of the fourth line 24 is connected to the branching connector 22b for connecting the second line 22. The fourth line 24 has such elements as a foreign matter removing filter 24a and a physiological salt solution container connecting needle 24b arranged as viewed from the connector 22b.

The plasma collecting bag 25 includes a first tube 25a connected to the branching connector 21f located between the blood-collection needle 29 and the pump tube 21g of the first line 21, and a second tube 25b connected to the branching connector 22a of the second line 22. The platelet collecting bag 26 includes a third tube 26a connected to the branching connector 22a of the second line 22. The buffy coat collecting bag 27 includes a fourth tube 27a connected to the branching connector 22d of the second line 22.

The tubes and the pump tubes used for forming the first to fourth lines and the tubes connected to the bags as described above are composed of such materials as polyvinyl chloride, polyethylene, polypropylene, polyester such as PET or PBT, ethylene-vinyl acetate copolymer, polyurethane, polyester elastomer, thermoplastic elastomer such as styrene-butadiene-styrene copolymer. Of all these component materials, polyvinyl chloride is the most preferable. If all the tubes are made of polyvinyl chloride, sufficient flexibility and plasticity can be obtained for easy handling. Also, this material is suitably used to cope with clogging caused by a clamp and the like. Component materials similar to these tube materials can also be used for forming the branching connectors. The pump tubes are required to have a sufficient strength to bear the pressure applied by the roller pump.

Each of the plasma collecting bag 25, the platelet collecting bag 26 and the buffy coat collecting bag 27 is composed of layers of flexible plastic sheets having the peripheral edges thereof fusion bonded (thermally or with high frequencies) or adhered. Soft polyvinyl chloride is the most preferable material for forming the bags 25, 26, 27. Plasticizers used for the soft polyvinyl chloride include, for example, di-(ethylhexyl) phthalate (DEHP), di-(n-decyl) phthalate (DnDP) and the like. The content of these plasticizers preferably ranges from approximately 30 to 70 wt .% to 100 wt .% of the polyvinyl chloride.

Other sheet materials that can be used for forming the bags 25, 26, 27 may be polyolefin, that is, a polymer formed by polymerizing or copolymerizing an olefin or di-olefin of ethylene, propylene, butadiene, isoprene or the like. More specifically, polyethylene, polypropylene, ethylene-vinyl acetate copolymer (EVA), polymer blend of EVA and various thermoplastic elastomers, etc. or an arbitrary combination thereof can be used. Still other applicable materials include polyester such as polyethylene terephthalate (PET), polybutylene terephthalate (PBT), poly-1,4-cydohexanedimethyl terephthalate (PCHT) and polyvinylidene chloride.

The sheet material used for the platelet collecting bag 26 is preferably superior in gas permeability for assuring an improved platelet shelf life. Such sheet materials preferably include, for example, the above-mentioned polyolefin or DnDP plasticized polyvinyl chloride, etc. Alternatively, using comparatively thin (say, about 0.1 to 0.5 mm thick, or especially, about 0.1 to 0.3 mm thick) materials is further preferable. The platelet collecting bag can be preliminarily filled with a platelet retainer such as physiological salt solution, GAC, PAS, PSM-1.

Figure 2:
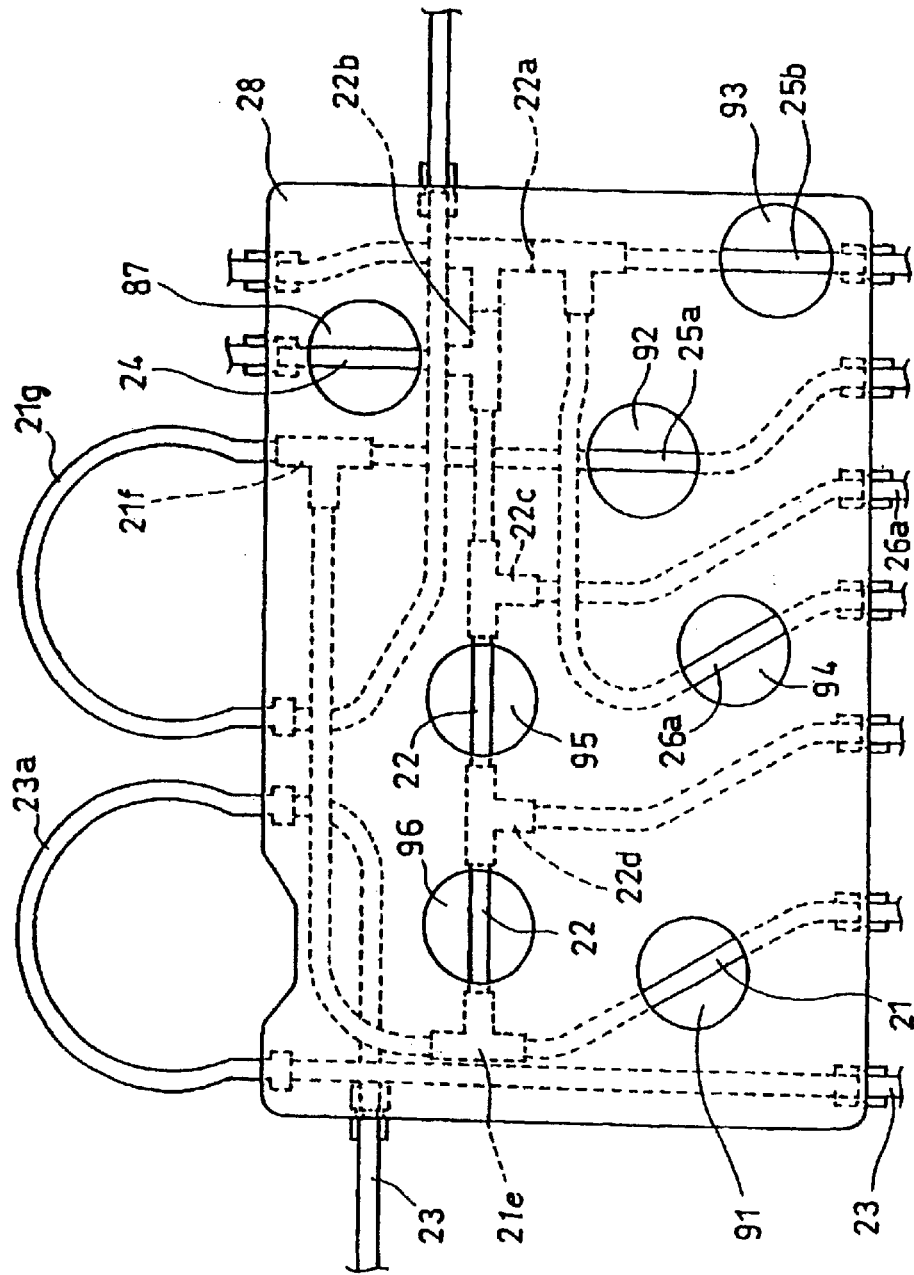
FIG. 2 is a plan view showing a cassette housing portion of the blood component collecting circuit shown in FIG. 1.

The essential portions of the blood component collecting circuit 2 are housed in a cassette as shown in FIG. 2. The blood component collecting circuit 2 includes a cassette housing 28 for partially containing or partially holding all the lines (first, second, third and fourth lines) and all the tubes (first, second, third and fourth tubes), that is, for partially fixing them. The cassette housing 28 has both ends of the first pump tube 21g and the second pump tube 23a fixed thereto. The pump tubes 21g, 23a extend from the cassette housing 28 in a loop to correspond to the shape of the roller pump. As a result, the first and the second pump tubes 21g, 23a can be readily mounted on the roller pump 11, 12.

Further, the cassette housing 28 includes a plurality of openings located therein. Specifically, located in the cassette housing 28 are a first opening 91 that exposes the portion of the first line 21 between the blood-collection needle and the pump tube 21g and can be intruded by the first flow path shutter means 81 of the blood component collecting apparatus 1, a second opening 92 that exposes the first tube 25a of the plasma collecting bag 25 and can be intruded by the second flow path shutter means 82 of the blood component collecting apparatus 1, a third opening 93 that exposes the second tube 25b of the plasma collecting bag 25 and can be intruded by the third flow path shutter means 83 of the blood component collecting apparatus 1, a fourth opening 94 that exposes the third tube of the platelet collecting bag 26 and can be intruded by the fourth flow path shutter means 84 of the blood component collecting apparatus 1, a fifth opening 95 that exposes the portion of the second line 22 between the centrifugal separator ( connector 22c) and the connector 22d for connecting the fourth tube 27a of the buffy coat collecting bag 27 to the second line 22 and can be intruded by the fifth flow path shutter means 85 of the blood component collecting apparatus 1, a sixth opening 96 that exposes the portion of the second line 22 between the connector of the first line 21 and the connector of the fourth tube 27a of the buffy coat collecting bag 27 (downstream of the connector of the second line 22 and the fourth tube 27a) and can be intruded by the sixth flow path shutter means 86 of the blood component collecting apparatus 1 and a seventh opening 97 that exposes the fourth line 24 and can be intruded by the seventh flow path shutter means 87 of the blood component collecting apparatus 1.

Also, the above-mentioned branching connectors are fixed to the inner surface of the cassette housing 28. Further, at least a reinforcing tube for holding the lines and tubes extended from the side of the housing and preventing the portions thereof in contact with the housing from being bent is arranged in the vicinity of the side of the cassette housing 28. The cassette housing 28 is box-shaped and contains the parts indicated by dashed lines. The cassette housing 28 is formed of a synthetic resin having a rigidity to a certain degree.

The blood component collecting apparatus 1 includes a mount (not shown) of the cassette housing. When the cassette housing 28 is mounted on the cassette housing mount of the blood component collecting apparatus 1, the lines and tubes exposed from the openings of the cassette housing 28 are automatically mounted on the corresponding flow path shutter means, respectively. As a result, the circuit can be easily mounted while performing rapid preparations for collecting the blood components. Also, the blood component collecting apparatus 1 has two pumps adjacent to the cassette housing mount. The pump tubes exposed from the cassette housing 28 can thus be easily mounted on the pump.

Figure 3:
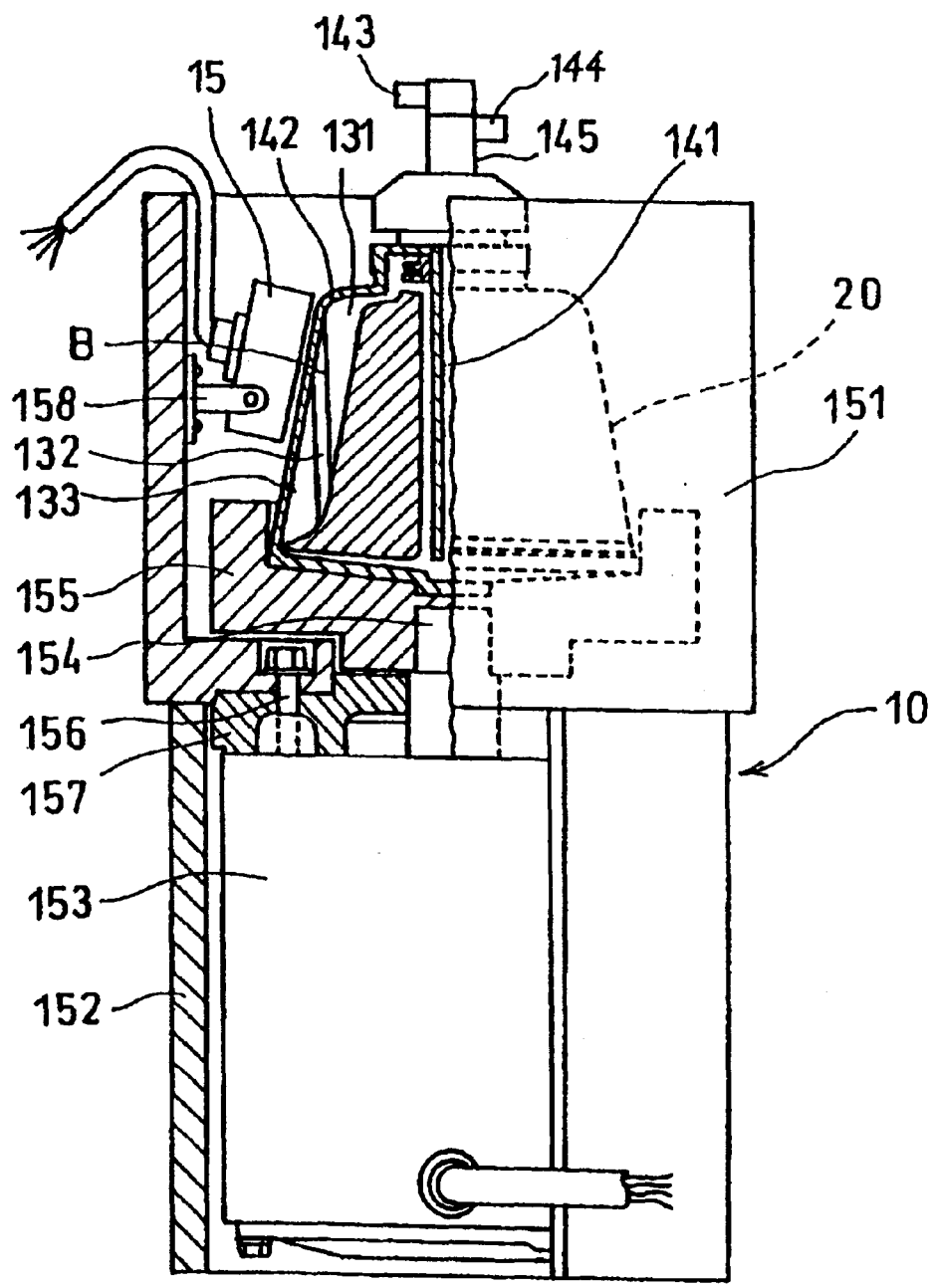
FIG. 3 is a partially cutaway sectional view showing the state in which a drive unit is mounted on a centrifugal separator used in a blood component collecting circuit.

The centrifugal separator 20 mounted in the blood component collecting circuit 2, which is usually called the centrifugal bowl, separates the blood into components by centrifugal force. The centrifugal separator 20, as shown in FIG. 3, includes a tubular member 141 extending vertically and having an inlet 143 formed at the upper end thereof, and a hollow rotor 142 sealed in fluid-tight at the upper portion 145 thereof and adapted to rotate around the tubular member 141. The rotor 142 has a flow path (blood storage space) along the bottom and the inner peripheral wall surface thereof. An outlet 144 is formed to communicate with the upper portion of the flow path. In this case, for example, the volume of the rotor 142 ranges from approximately 100 to 350 ml.

The rotor 142 is rotated under predetermined centrifugal conditions (rotational speed and rotation time) by the rotor drive unit 10 of the blood component collecting apparatus 1. These centrifugal conditions are used to set a pattern of the blood separated (the number of blood components to be separated, for example) in the rotor 142. According to this embodiment, as shown in FIG. 3, the centrifugal conditions are set such that the blood is separated into a plasma layer 131, a buffy coat layer 132 and a red cell layer 133 laminated from the inside within the flow path of the rotor 142.

Figure 4:
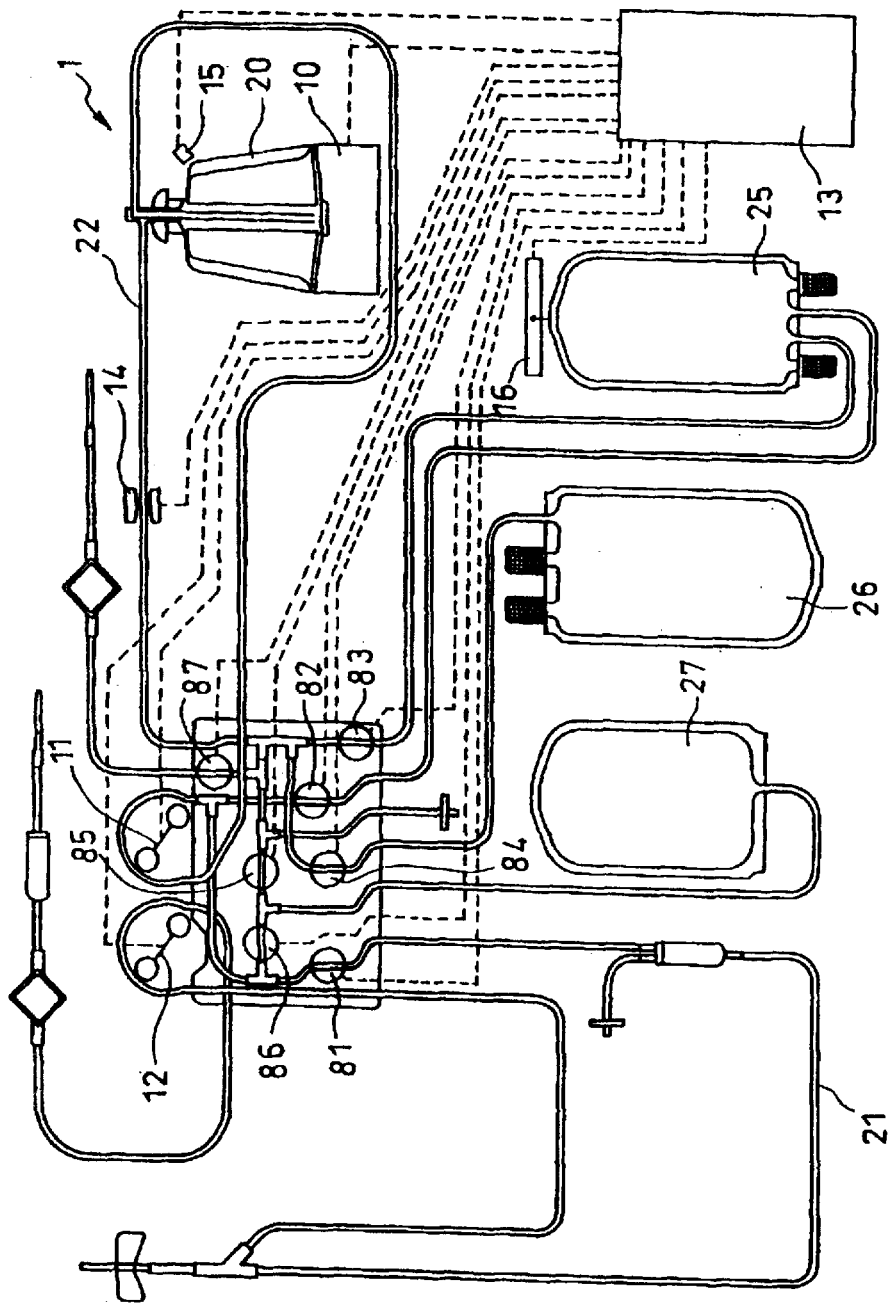
FIG. 4 is a schematic drawing of a blood component collecting apparatus according to an embodiment of the invention having a blood component collecting circuit mounted thereon.

Referring to FIG. 4, the blood component collecting apparatus 1 according to this invention will be described.

The blood component collecting apparatus 1 is provided with the centrifugal separator drive unit 10 for rotating the rotor 142 of the centrifugal separator 20, the first liquid supply pump 11 for the first line 21, the second liquid supply pump 12 for the third line 23, a plurality of the flow path shutter means 81, 82, 83, 84, 85, 86, 87 for opening/closing the flow paths of the blood component collecting circuit 2, and the controller 13 for controlling the centrifugal separator drive unit 10, the first liquid supply pump 11, the second liquid supply pump 12 and the flow path shutter means. Further, the blood component collecting apparatus 1 comprises a turbidity sensor 14 mounted on the portion of the second line 22 between the centrifugal separator and the connector 22a for connecting the second tube 25b to the second line 22, an optical sensor 15 mounted above the centrifugal separator 20 and a weight sensor 16 for detecting the weight of the plasma collecting bag 25.

The controller 13 includes two pump controllers (not shown) for the first liquid supply pump 11 and the second liquid supply pump 12 respectively. The control mechanism of the controller 13 is electrically connected to the first liquid supply pump 11 and the second liquid supply pump 12 through a pump controller. The drive controller of the centrifugal separator drive unit 10 is electrically connected to the controller 13. The flow path shutter means 81, 82, 83, 84, 85, 86, 87 are all connected to the controller 13 for controlling the respective opening/closing operations. Also, the turbidity sensor 14, the optical sensor 15 arranged above the centrifugal separator 20 and the weight sensor 16 for detecting the weight of the plasma collecting bag 25 are electrically connected to the controller 13 to which the signals output from these components are applied. The control mechanism of the controller 13 is configured of, for example, a microcomputer and the detection signals from the weight sensor 16, the optical sensor 15 and the turbidity sensor 14 are applied to the controller 13 from time to time. The controller 13 controls the start and stop of the rotation and rotational direction (forward/backward) of each pump based on the signals from the turbidity sensor 14, the optical sensor 15 and the weight sensor 16 while controlling the opening/closing operation of the flow path shutter means and the centrifugal separator drive unit 10.

The first flow path shutter means 81 is provided for opening/closing the portion of the first line 21 between the blood-collection needle and the pump tube 21g. The second flow path shutter means 82 is provided for opening/closing the first tube 25a communicated with the plasma collecting bag 25. The third flow path shutter means 83 is provided for opening/closing the second tube 25b communicated with the plasma collecting bag 25. The fourth flow path shutter means 84 is provided for opening/closing the third tube communicated with the platelet collecting bag 26. The fifth flow path shutter means 85 is provided for opening/closing the portion of the second line 22 between the centrifugal separator and the connector 22d for connection between the second line 22 and the fourth tube 27a communicated with the buffy coat collecting bag 27. The sixth flow path shutter means 86 is provided for opening/closing the portion of the second line 22 between the connector 21e of the fist line 21 and the connector 22d of the fourth tube 27a (downstream of the connector of the second line 22 and the fourth tube 27a). The seventh flow path shutter means 87 is provided for opening/closing the fourth line 24. Each of these flow path shutter means includes a line or tube insertion member having a clamp adapted to be energized by, for example, a solenoid, an electric motor, a (hydraulic or pneumatic) cylinder or other drive source. Specifically, an electromagnetic clamp operated by the solenoid is preferable. The clamp provided with the flow path shutter means is operated based on the signal from the controller 13.

The drive unit 10, as shown in FIG. 3, includes a rotor drive unit housing 151 for containing the centrifugal separator 20, a pedestal 152, a motor 153 constituting a drive source and a circular rest 155 for holding the centrifugal separator 20. The housing 151 is mounted and fixed on the pedestal 152. Also, a motor 153 is fixed to the lower surface of the housing 151 with a bolt 156 via a spacer 157. The forward end of the rotary shaft 154 of the motor 153 is fitted such that the rest 155 rotates coaxially and integrally with the rotational shaft 154. The upper portion of the rest 155 has a recess formed therein to which the bottom of the rotor 142 is fitted. Also, the upper portion 145 of the centrifugal separator 20 is fixed to the housing 151 with a fixing member not shown. Once the motor 153 for the rotor drive unit 10 is started, the rest 155 and the rotor 142 fixed thereto are rotated at a rotational speed, for example, ranging from 3000 to 6000 rpm.

The inner wall of the rotor drive unit housing 151 has an optical sensor 15 that is fixedly mounted thereon with a mounting member 158 for optically detecting the boundaries of the separated blood components (for example, the boundary B between the plasma layer 131 and the buffy coat layer 132, and the boundary between the buffy coat layer 132 and the red cell layer 133) in the rotor 142. The above optical sensor 15 is adapted to scan the outer peripheral surface of the rotor 142 in vertical direction. This sensor 15 includes a light source for emitting a light beam toward the shoulder of the centrifugal separator 20 and a photo-detector for receiving the light reflected and returned from the centrifugal bowl. Specifically, a light emitting element like LED and a light receiving element are linearly arranged. The light emitted from the light emitting element and reflected from a blood component is received by the light receiving element, such that the amount of the received light is subjected to photoelectric conversion. The intensity of the reflected light varies depending on the separated blood component (for example, the boundary B between the plasma layer 131 and the buffy coat layer 132). The position on the light receiving element that has changed in the received light amount, therefore, is detected as a corresponding position of the boundary B. More specifically, arrival of the buffy coat layer at a light passage is detected based on the difference in the received light amount between the time when the centrifugal separator 20 is filled with a transparent liquid (plasma or water) at a point of the light passage and the time when it is filled with the buffy coat layer at the particular point of the light passage. The point where the buffy coat layer is detected is adjusted by changing the point of light passage in the bowl. The point of light passage, once determined, is usually fixed there.

The turbidity sensor 14 is used for detecting the turbidity of the fluid flowing through the second line 22 and outputs a voltage value corresponding to the detected turbidity. Specifically, a low voltage value is output when the turbidity is high, while a high voltage value is output when the turbidity is low.

Each of the first liquid supply pump 11 mounted the pump tube 21g of the first line 21 and the second liquid supply pump 12 mounted the pump tube 23a of the third line 23 are preferably formed as a pump kept out of contact with the blood such as a roller pump or peristaltic pump. Also, a pump that can supply the blood in either direction is used as the first liquid supply pump 11 (blood pump). Specifically, a roller pump capable of rotating forward/backward is used.

The controller 13 controls the centrifugal separator drive unit 10, the first liquid supply pump 11, the second liquid supply pump 12 and a plurality of the flow path shutter means in order to execute a platelet collecting operation. The platelet collecting operation includes a plurality (at least two times, preferably, twice to seventh times, more preferably, three times to sixth times) of plasma collecting-circulation steps including a plasma collecting step for collecting blood added anticoagulant by starting the first and the second liquid supply pumps 11, 12 and collecting a predetermined amount of plasma in the plasma collecting bag 25 by activating the centrifugal separator drive unit, and a plasma circulation step for temporarily suspending blood-collection subsequent to the plasma collecting step and circulating the plasma contained in the plasma collecting bag to the centrifugal separator 20 by activating the centrifugal separator drive unit 10; and, subsequent to a plurality of plasma collecting-circulation steps, to execute a platelet collecting step for collecting platelets released from the centrifugal separator 20 in the platelet collecting bag 26 by accelerating the plasma circulation rate by the first liquid supply pump 11, which is followed by a blood returning step for returning the blood contained in the centrifugal separator 20.

Further, the controller 13 of the blood component collecting apparatus 1 according to this embodiment controls the centrifugal separator drive unit 10, the first liquid supply pump 11, the second liquid supply pump 12 and a plurality of the flow path shutter means such that the platelet collecting operation is executed at least twice, or specifically, twice to fifth times, more preferably, three times.

Specifically, the first plasma collecting-circulation step including the first plasma collecting step and the first plasma circulation step is executed. In the first plasma collecting step, the blood containing the added anticoagulant is collected by starting the first and the second liquid supply pumps 11, 12 and the centrifugal separator drive unit 10 is activated to collect a first predetermined amount of plasma in the plasma collecting bag 25. This step is followed by the first plasma circulation step in which the blood-collection is temporarily suspended and the centrifugal separator drive unit 10 is activated to circulate the plasma contained in the plasma collecting bag to the centrifugal separator 20. Then a second plasma collecting-circulation step including the second plasma collecting step and the second plasma circulation step is executed. In the second plasma collecting step, the first and the second liquid supply pumps 11, 12 are started to collect the blood added anticoagulant and the centrifugal separator drive unit 10 is activated to collect the plasma until the amount of plasma contained in the plasma collecting bag 25 reaches a second predetermined amount (total amount) that is larger than the first predetermined amount. The second plasma collecting step is followed by the second plasma circulation step in which the blood-collection is temporarily suspended and the centrifugal separator drive unit 10 is activated to circulate the plasma contained in the plasma collecting bag 25 to the centrifugal separator 20.

The controller 13 of the blood component collecting apparatus 1 according to this embodiment executes a third plasma collecting-circulation step subsequent to the second plasma circulation step. The third plasma collecting-circulation step includes a third plasma collecting step and a third plasma circulation step. In the third plasma collecting step, the first and second liquid supply pumps 11, 12 are started to collect the blood added anticoagulant, and the centrifugal separator drive unit 10 is activated to collect the plasma until the amount thereof contained in the plasma collecting bag 25 reaches a third predetermined amount (total amount) that is larger than the second predetermined amount. The above third plasma collecting step is followed by the third plasma circulation step in which the blood-collection is temporarily suspended and the centrifugal separator drive unit 10 is activated to circulate the plasma contained in the plasma collecting bag to the centrifugal separator 20.

Further, the controller 13 of the blood component collecting apparatus 1 executes a fourth plasma collecting-circulation step upon completion of the third plasma circulation step. The fourth plasma collecting-circulation step includes a fourth plasma collecting step and a fourth plasma circulation step. In the fourth plasma collecting step, the first and the second liquid supply pumps 11, 12 are started to collect the blood added anticoagulant, and the centrifugal separator drive unit 10 is activated to collect the plasma until the amount thereof contained in the plasma collecting bag 25 reaches a fourth predetermined amount (total amount) that is larger than the third predetermined amount. The fourth plasma collecting step is followed by the fourth plasma circulation step, in which the blood-collection is temporarily suspended and the centrifugal separator drive unit 10 is activated to circulate the plasma contained in the plasma collecting bag 25 to the centrifugal separator 20.

The second predetermined amount is larger than the first predetermined amount because the total amount of plasma contained in the plasma collecting bag 25 is increased. Therefore, the amount of the plasma collected in the second plasma collecting step is not necessarily larger than the that of the plasma collected in the first plasma collecting step. Therefore, the amount of the plasma collected in the third plasma collecting step is not necessarily larger than the that of the plasma collected in the second plasma collecting step. Therefore, the amount of the plasma collected in the fourth plasma collecting step is not necessarily larger than the that of the plasma collected in the third plasma collecting step. In other words, an arbitrary amount of the plasma can be collected in each plasma collecting step. For the controlling purpose, the first, second, third and fourth predetermined amounts are stored in the controller, each of which is compared with the weight signal detected by the weight sensor. When it is detected that the weight of the plasma contained in the plasma collecting bag has reached a particular predetermined value, each plasma collecting step is terminated.

Further, the controller 13 of the blood component collecting apparatus 1 according to this embodiment executes a fifth plasma collecting-circulation step subsequent to the fourth plasma circulation step. The fifth plasma collecting-circulation step similarly includes a fifth plasma collecting step and a fifth plasma circulation step. In the fifth plasma collecting step, the first and the second liquid supply pumps 11, 12 are started to collect the blood added anticoagulant, and the centrifugal separator drive unit 10 is activated to collect the plasma contained in the plasma collecting bag 25. The fifth plasma collecting step is followed by the fifth plasma circulation step in which the blood-collection is temporarily suspended and the centrifugal separator drive unit 10 is activated to circulate the plasma contained in the plasma collecting bag 25 to the centrifugal separator 20. In the fifth plasma collecting step using a boundary sensor, the weight of the plasma bag is not detected.

Subsequent to the platelet collecting step and prior to the start of the blood returning step, the controller 13 of the blood component collecting apparatus 1 according to this embodiment executes a buffy coat collecting step in which the plasma circulation rate by means of the first liquid supply pump 11 is increased to exceed the final rate in the platelet collecting step such that the buffy coat is released from the centrifugal separator 20 into a buffy coat collecting bag 27. The buffy coat collecting step is not limited to the above-mentioned method. Alternatively it can be executed such that the plasma circulation rate by means of the first liquid supply pump 11 is maintained at the final rate in the platelet collecting step while decreasing the rotational speed of the rotor of the centrifugal separator 20. Further, the buffy coat collecting step can be executed by increasing the plasma circulation rate by means of the first liquid supply pump to exceed the final rate in the platelet collecting step while decreasing the rotational speed of the rotor of the centrifugal separator.

After completing the buffy coat collecting step, the first liquid supply pump 11 and a plurality of the flow path shutter means are controlled such that the buffy coat returning step for returning the collected buffy coat into the centrifugal separator 20 is executed prior to the subsequent blood-collection step.

Specifically, an anticoagulant is added to the whole blood by a predetermined ratio (1/6 to 1/20, or specifically, 1/10 of the whole blood), and the resultant blood is fed to the centrifugal separator 20 through the first line 21 at a predetermined rate (250 ml/min or less, preferably, 150 to 40 ml/min or less, or specifically, 60 ml/min or less). The centrifugal separator 20 is rotated at a predetermined rotational speed (3000 to 6000 rpm, or preferably, 4700 to 4800 rpm) to separate the blood into components including plasma, buffy coat and red cells. The plasma that has overflowed the centrifugal separator 20 is collected in the plasma collecting bag. At a time point when a predetermined amount (10 to 150 ml, or preferably 20 to 30 ml) of plasma is collected, the blood supply is stopped. Then, the plasma is returned to the centrifugal separator 20 through the first and second lines 21, 22 under predetermined conditions (at a rate higher than that for blood-collection, i.e. 60 to 250 ml/min for 10 to 90 sec, or specifically, 200 ml/min for 30 sec. for the first circulation, and 120 ml/min for 30 sec. for the second and subsequent circulation). Each time when the plasma reaches a predetermined amount (not more than 150 ml collected as measured from the final circulation) before the end of blood-collection, the plasma circulation is repeated. When the buffy coat in the centrifugal separator 20 reaches a predetermined radius (specifically, 30 to 40 mm), the blood-collection is suspended and the plasma is returned to the centrifugal separator 20 through the first and second lines 21, 22 under predetermined conditions (60 to 250 ml/min for 10 to 90 sec specifically, 120 to 140 ml/min for 30 sec.). Then, the whole blood added anticoagulant is fed again under predetermined conditions (the amount of the collected blood :0 to 2500/Hct % [ml], or specifically, 1200 to 1400/Hct % [ml]), after which the plasma is returned to the centrifugal separator 20 through the first and second lines 21, 22 under the predetermined conditions. The acceleration rate is increased stepwise under predetermined conditions (stepwise acceleration ranging from 0.1 to 99 ml/min/sec, or specifically, 10 ml/min/sec) until the platelet collecting rate reaches (60 to 250 ml/min, or actually, 200 ml/min). The platelets released from the centrifugal separator 20 are then collected in the platelet collecting bag 26. Further, after collecting the platelets, the blood circulation rate (at 60 to 250 ml/min., or specifically, 200 ml/min) is maintained while reducing the rotation of the centrifugal separator 20 (by about 100 to 300 rpm, or preferably down to 4500 to 4600 rpm). In this way, the released buffy coat is collected and supplied to the centrifugal separator 20 prior to the next blood-collection cycle. The buffy coat can alternatively be collected by increasing the blood circulation rate to a predetermined level (not less than the platelet collecting rate, or preferably 60 to 250 ml/min., specifically, 205 ml/min.).

The blood component collecting process (first platelet collecting operation) by the blood component collecting apparatus 1 according to this embodiment will be explained with reference to FIGS. 4, 5 to 10. In this embodiment, the platelet collecting operation is repeated three times, and prior to the blood returning step, the buffy coat collecting step is executed after each platelet collecting step other than the last one. Also, prior to the next blood-collection step, the buffy coat returning step is performed to return the buffy coat to the centrifugal separator 20.

First, the third line 23 and the blood-collection needle 29 are primed with an anticoagulant and the needle is inserted into the donor.

Figure 5:
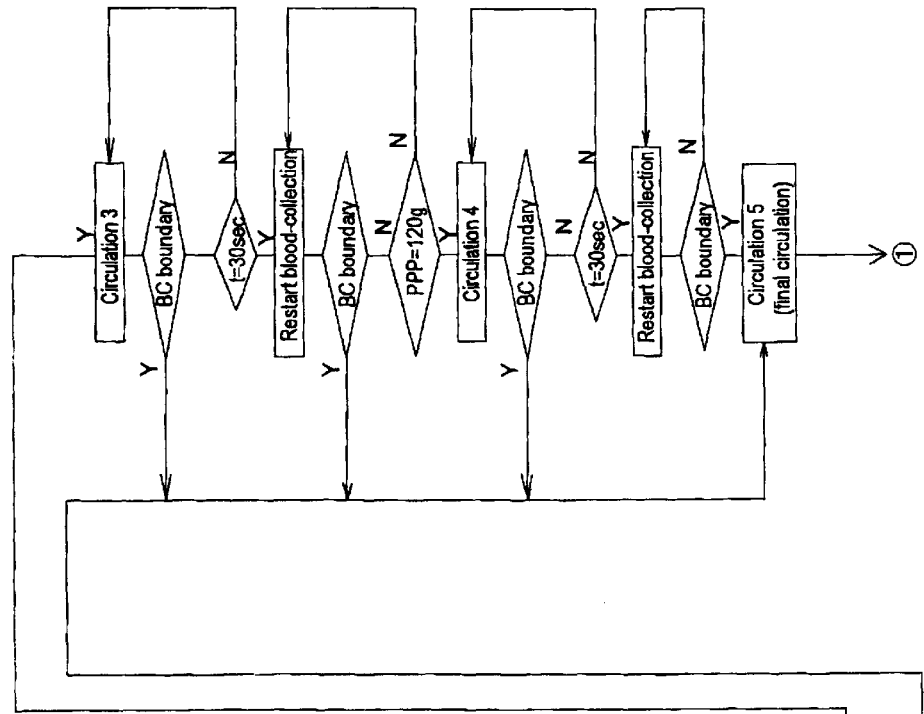
FIG. 5 is a flowchart representing the operation of a blood component collecting apparatus according to the invention.
Figure 5:
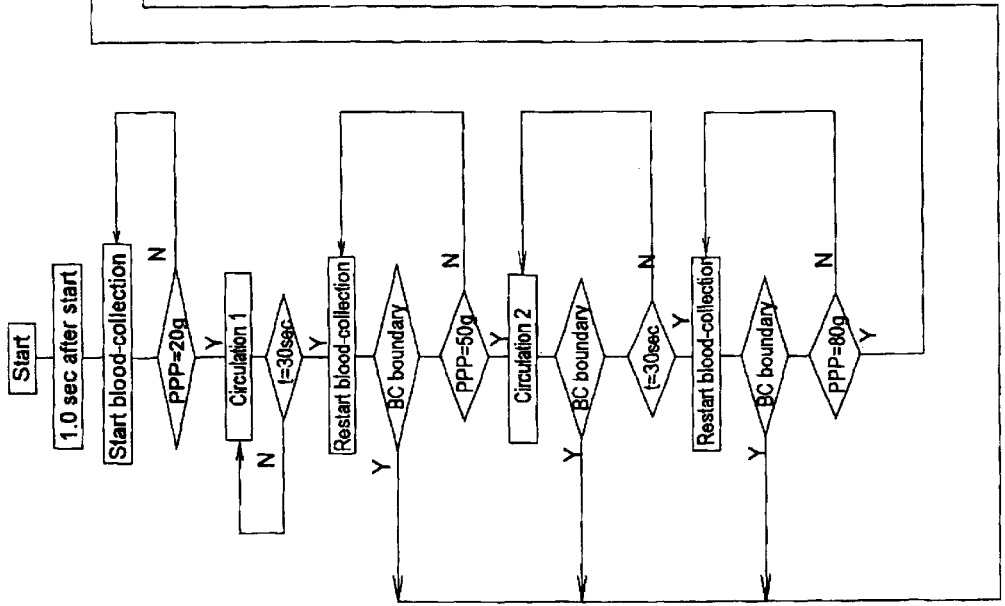

As shown in FIG. 5, a first plasma collecting step is executed in which the blood added anticoagulant is collected by starting the first and second liquid supply pumps 11, 12 and a first predetermined amount of plasma obtained from the blood is collected into the plasma collecting bag 25 by working the centrifugal separator drive unit 10.

When the first blood-collection starts, the blood pump 11 starts collecting the blood at a predetermined rate (for example, 60 ml/min). At the same time, the second pump constituting an anticoagulant pump supplies the anticoagulant (for example, ACD-A solution) at a predetermined rate (for example, 1/10 of the blood pump rate). The blood drawn from the donor is mixed with the ACD solution, flows through the first line 21, the chamber and the first flow path shutter means 81, and enters the centrifugal separator 20. At the above time point, the sixth flow path shutter means 86, the fifth flow path shutter means 85, the second flow path shutter means 82, the third flow path shutter means 83 and the seventh flow path shutter means 87 are closed. Meanwhile the first flow path shutter means 81 and the fourth flow path shutter means 84 are open. When the blood added ACD is fed to the centrifugal separator 20, the sterilized air that has stayed in the centrifugal separator 20 flows through the second line 22 and the flow path shutter means 84 into the platelet collecting bag 26. Simultaneously with the start of the blood-collection, the centrifugal separator 20 starts rotating at a predetermined speed.(say, 4800 rpm) while being supplied with the blood added ACD. In the centrifugal separator 20, therefore, the blood is centrifugally separated into a plasma layer, a buffy coat layer (BC layer) and a red cell layer formed from the inside. When the blood added ACD is supplied in excess of (about 270 ml) the capacity of the separator, the centrifugal separator 20 is completely filled with the blood, by which the plasma overflows through the outlet of the centrifugal separator 20. The turbidity sensor 14 mounted on the second line 22 connected to the outlet of the centrifugal separator 20 detects the change in the fluid flowing through the line from air to plasma. The controller 13 thus closes the fourth flow path shutter means 84 in response to the detection signal of the turbidity sensor 14 and opens the third flow path shutter means 83 to collect the plasma in the plasma collecting bag 25. The weight of the plasma collecting bag 25 is preliminarily measured by the weight sensor 16, and the measurement value has been applied to the controller 13. When the weight of the plasma collected in the plasma collecting bag 25 is increased to a predetermined amount (for example, 10 to 150 g, or 20 g), the controller 13 closes the first flow path shutter means 81 and opens the second flow path shutter means 82. Then the process proceeds to the first plasma circulation step.

In the first plasma circulation step, the blood-collection is temporarily suspended and the centrifugal separator drive unit 10 is activated, such that the plasma contained in the plasma collecting bag 25 is circulated to the centrifugal separator 20.

Upon start of the first plasma circulation step, the controller 13 keeps the first flow path shutter means 81 closed and the second flow path shutter means 82 opened, stops the ACD pump 12 and starts the blood pump 11 at a predetermined rate (60 to 250 ml/min, for example, 200 m/min). The plasma collected in the plasma collecting bag 25 thus is fed through the second flow path shutter means 82 to the centrifugal separator 20 rotating at 4800 rpm. At the same time, the plasma flowing from the centrifugal separator 20 enters the plasma collecting bag 25 through the turbidity sensor 14 and the third flow path shutter means 83. With the lapse of a predetermined length of time (10 to 90 sec, for example, 30 sec) from the start of the first plasma circulation step, the controller 13 closes the second flow path shutter means 82, opens the first flow path shutter means 81, and proceeds to the second plasma collecting step. The first plasma circulation step is executed preferably at the flow rate of 60 ml/min or more for at least 10 seconds.

In the second plasma collecting step, the first and second liquid supply pumps 11, 12 are started to collect the blood added anticoagulant, and the centrifugal separator drive unit 10 is activated to collect the plasma until the collected amount in the plasma collecting bag 25 reaches a second predetermined amount that is larger than the first predetermined amount (by 10 to 150 g).

Specifically, the blood pump 11 is activated to collect the blood at a predetermined rate (for example, 60 ml/min). At the same time, the second pump constituting an anticoagulant pump supplies the coagulant (for example, ACD-A solution) at a predetermined rate (say, 1/10 of the rate of the blood pump). The blood drawn from the donor is mixed with the ACD solution, and flows into the centrifugal separator 20 rotating at a predetermined speed (say, 4800 rpm) for collecting the plasma in the plasma collecting bag 25. The weight of the plasma collecting bag 25 is measured by the weight sensor 16 and applied to the controller 13. When the weight of the plasma collected in the plasma collecting bag 25 reaches the second predetermined amount (10 to 150 g larger than the first predetermined amount, or specifically, the second predetermined amount may be set to 50 g), the controller 13 closes the first flow path shutter means 81, opens the second flow path shutter means 82, and proceeds to the second plasma circulation step.

In the second plasma circulation step, the blood-collection is temporarily suspended and the centrifugal separator drive unit 10 is activated to circulate the plasma in the plasma collecting bag 25 to the centrifugal separator 20. In the process, the blood pump operates at a predetermined rate lower than that in the first plasma circulation step, for example, at 120 ml/min for about 30 sec. The second plasma circulation is preferably conducted at a rate ranging from 60 to 250 ml/min for 10 to 90 seconds. In other words, the second plasma circulation is conducted preferably at the rate of at least 60 ml/min for not shorter than ten seconds.

Subsequent to the second plasma circulation step, the third plasma collecting step is executed for collecting the blood added anticoagulant. At the same time, the centrifugal separator drive unit 10 is activated to collect the plasma until the collected amount of the plasma in the plasma collecting bag 25 reaches a third predetermined amount that is larger than the second predetermined amount (by 10 to 150 g, or specifically, the third predetermined amount may be set to 80 g).

In the third plasma collecting step, the first liquid supply pump 11 starts blood-collecting at a predetermined rate (say, 60 ml/min). In the process, the second pump constituting an anticoagulant pump supplies an anticoagulant (such as the ACD-A solution) at a predetermined rate (say, 1/10 of the rate of the blood pump). The blood drawn from the donor is mixed with the ACD solution, and flows into the centrifugal separator 20 rotating at a predetermined speed (say, 4800 rpm) for collecting the plasma in the plasma collecting bag 25. The weight of the plasma collecting bag 25 is measured by the weight sensor 16, and the weight signal representing the measurement is applied to the controller 13. Therefore, when the weight of the plasma collected in the plasma collecting bag 25 reaches the third predetermined amount, the controller 13 closes the first flow path shutter means 81, opens the second flow path shutter means 82, and proceeds to the third plasma circulation step.

In the third plasma circulation step, the blood-collection is temporarily suspended and the centrifugal separator drive unit 10 is activated to circulate the plasma in the plasma collecting bag 25 to the centrifugal separator 20. The blood pump is operated at a predetermined rate lower than that in the first plasma circulation step, say, at 120 ml/min for about 30 sec. The third plasma circulation is preferably performed at a rate ranging from 60 to 250 ml/min for 10 to 90 seconds. In other words, the third plasma circulation is preferably executed at the rate of at least 60 ml/min for not shorter than 10 seconds.

Upon completion of the third plasma circulation step, a fourth plasma collecting step is executed. In this step, the blood added anticoagulant is collected and the centrifugal separator drive unit 10 is activated to collect the plasma until the collected amount of the plasma in the plasma collecting bag 25 reaches a fourth predetermined amount (10 to 150 g larger than the third predetermined amount, or specifically the fourth predetermined amount may be set to 120 g) larger than the third predetermined amount.

Specifically, the first liquid supply pump 11 is activated to start blood-collection at a predetermined rate (say, 60 ml/min). At the same time, the second pump constituting an anticoagulant pump supplies an anticoagulant (such as the ACD-A solution) at a predetermined rate (for example, 1/10 of the blood pump rate, for example). The blood supplied from the donor is mixed with the ACD solution and flows into the centrifugal separator 20 rotating at a predetermined speed (say, 4800 rpm), by which the plasma is collected in the plasma collecting bag 25. The weight of the plasma collecting bag 25 is measured by the weight sensor 16, and the weight signal representing the weight measurement is applied to the controller 13. As a result, when the weight of the plasma collected in the plasma collecting bag 25 reaches the fourth predetermined amount, the controller 13 closes the first flow path shutter means 81, opens the second flow path shutter means 82, and proceeds to the fourth plasma circulation step.

In the fourth plasma circulation step, the blood-collection is temporarily suspended and the centrifugal separator drive unit 10 is activated to circulate the plasma in the plasma collecting bag 25 to the centrifugal separator 20. In the process, the blood pump is activated at a predetermined rate lower than that in the first plasma circulation step, say, at 120 ml/min for about 30 sec. The fourth plasma circulation is preferably conducted at a rate of 60 to 250 ml/min for about 10 to 90 seconds. In other words, the fourth plasma circulation is preferably performed at a rate of at least 60 ml/ min for at least ten seconds.

Figure 7:
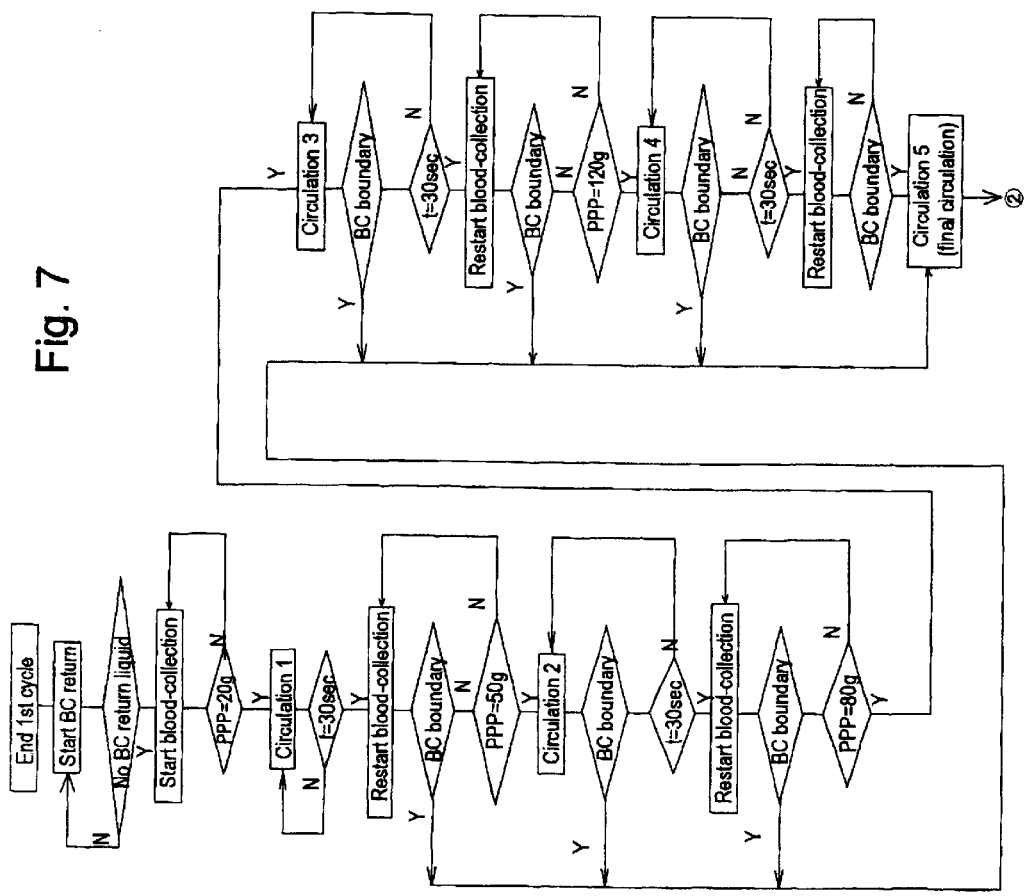
FIG. 7 is a flowchart representing the operation of a blood component collecting apparatus according to the invention.
Figure 9:
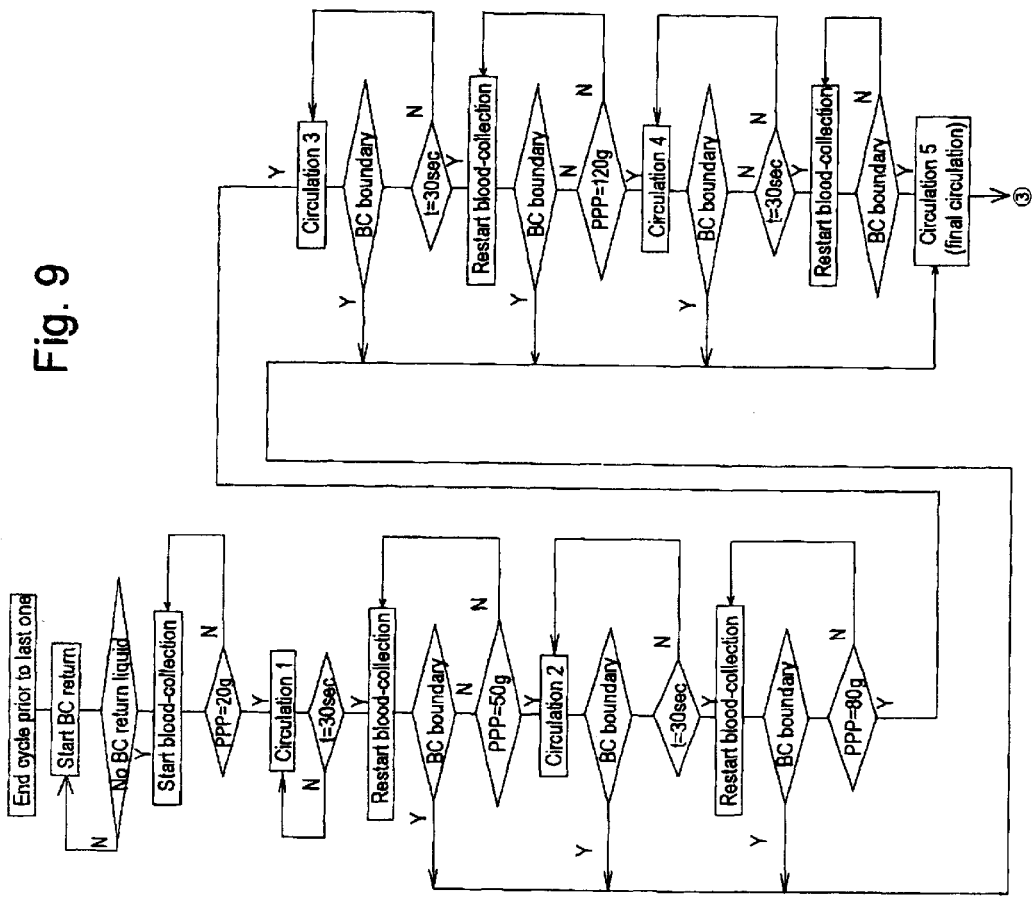
FIG. 9 is a flowchart representing the operation of a blood component collecting apparatus according to the invention.

Upon completion of the fourth plasma circulation step, a fifth plasma collecting step is executed to collect the blood added anticoagulant. The centrifugal separator drive unit 10 is activated to collect the plasma in the plasma collecting bag 25. Specifically, the first liquid supply pump 11 starts blood-collection at a predetermined rate (say, 60 ml/min). At the same time, the second pump constituting the anticoagulant pump supplies an anticoagulant (such as the ACD-A solution) at a predetermined rate (say, 1/10 of the blood pump rate). The blood drawn from the donor is mixed with the ACD solution and flows into the centrifugal separator 20 rotating at a predetermined speed (say, 4800 rpm), by which the plasma is collected in the plasma collecting bag 25. Normally, when the optical sensor 15 detects the buffy coat layer in the separator accompanied with the increase in the amount of the plasma in the bag, the detection signal is applied to the controller 13, which in turn closes the first flow path shutter means 81 and opens the second flow path shutter means 82. Then the process proceeds to a fifth plasma circulation step. In the fifth plasma collecting step, the plasma continues to be collected until the buffy coat (BC boundary the boundary between the plasma layer and the buffy coat layer) is detected by the sensor. In the apparatus according to this embodiment, as shown in the flowcharts of FIGS. 5, 7, 9, the BC boundary is detected in the first to fourth plasma collecting steps. Upon detection of the BC boundary in the first to fourth plasma collecting steps, the plasma collecting operation is suspended, and the process proceeds to what apparently is assumed to be a fifth plasma circulation step (not actually the fifth circulation step but the final circulation step).

In the fifth plasma circulation step (final plasma circulation step), the blood-collection is temporarily suspended and the centrifugal separator drive unit 10 is activated to circulate the plasma in the plasma collecting bag to the centrifugal separator 20. The blood pump operates at a predetermined rate of, for example, 120 ml/min for 30 sec. The fifth plasma circulation is performed at a rate of 60 to 250 ml/min for 10 to 90 seconds, and preferably at a rate of at least 60 ml/min for not less than 10 seconds. Subsequent to this circulation step, the process proceeds to the program referred to as ① in FIG. 6 to perform the blood-collection for boundary adjustment.

Figure 6:
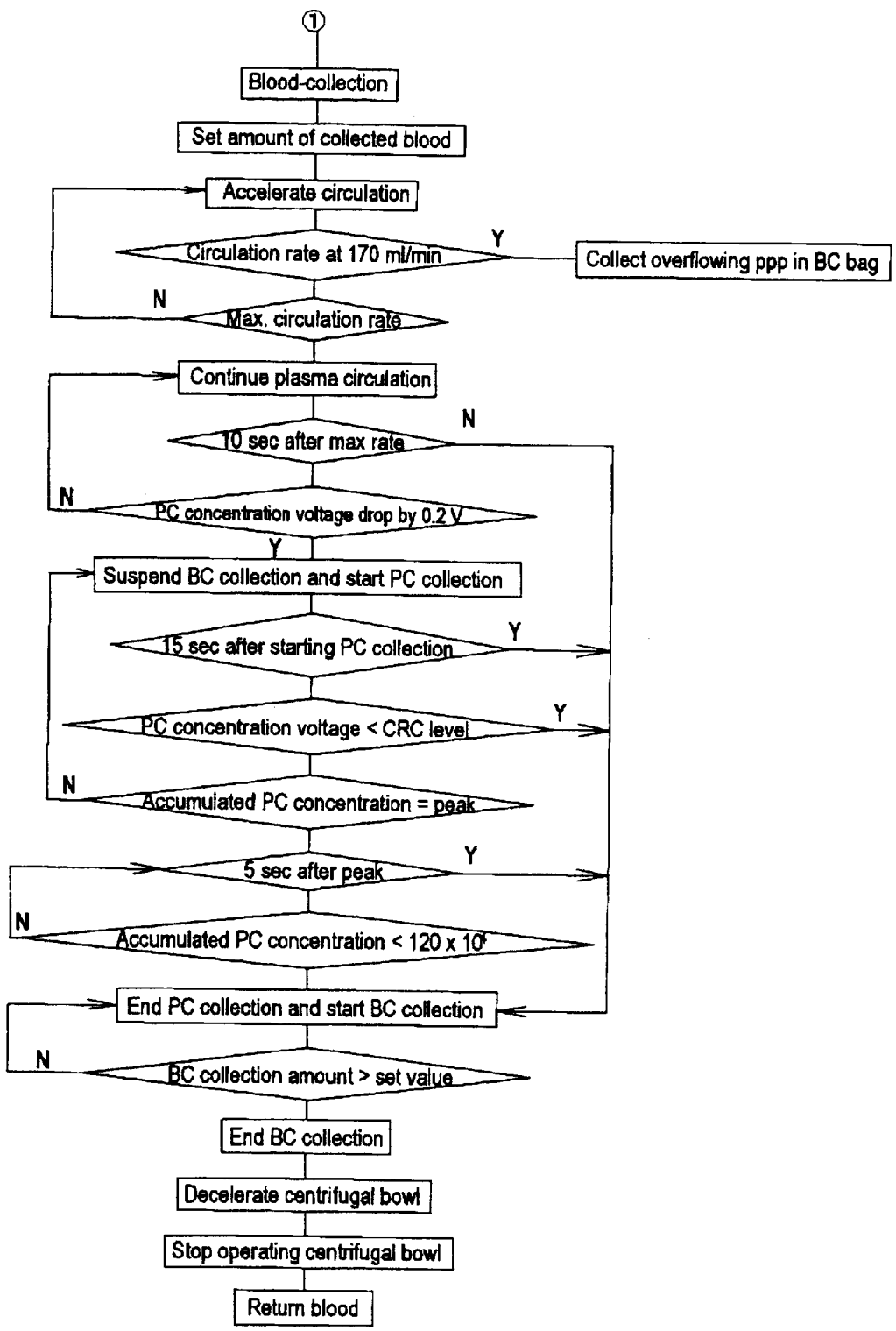
FIG. 6 is a flowchart for explaining the operation of a blood component collecting apparatus according to the invention.

As shown in FIG. 6, the blood-collection step for boundary adjustment can be regarded as a step of collecting a small amount of plasma. In this step, in order to keep the position of the buffy coat layer constant irrespective of the donor in the subsequent platelet collecting step, the blood is collected such that only a predetermined amount of red cells is obtained. The amount of supplied red cells is defined as the value derived from dividing the collected amount of blood by the hematocrit value of the donor. Practically about 12 ml of the blood is collected. This blood-collection is also started at a predetermined rate (say, 60 ml/min) by the first liquid supply pump 11. In the process, the second pump constituting the anticoagulant pump also supplies an anticoagulant (such as the ACD-A solution) at a predetermined rate (for example, 1/10 of the blood pump rate, for example). The blood collected from the donor is mixed with the ACD solution and flows into the centrifugal separator 20 rotating at a predetermined speed (say, 4800 rpm) to collect a small amount of plasma. The controller 13 calculates the blood collecting time based on the set collection amount and the pump rate, and terminates the blood-collection when the blood collecting time expires. Then the controller 13 closes the first flow path shutter means 81, opens the second flow path shutter means 82, and proceeds to a platelet collecting step.

Upon completion of the above-mentioned steps, the platelet collecting step is executed to accelerate the plasma circulation rate by the first liquid supply pump 11. Then platelets are released from the centrifugal separator 20 and collected in the platelet collecting bag 26. The platelet collecting step is also known as the acceleration step. In this step, the controller 13 activates the blood pump so as to accelerate the blood pump from the same rate as that in the fourth circulation step to 200 ml/min stepwise by 10 ml/min at a predetermined time interval (say, every one second). When the rate reaches 200 ml/min, it is maintained until completion of the platelet collecting step.

Upon start of the platelet collecting step, the turbidity of the liquid passing through the turbidity sensor 14 is detected and output as a voltage value by the sensor. The output signal is applied to the controller 13. When the blood pump rate increases to reach a rate ranging from about 160 to 200 ml/min, the platelets contained in the buffy coat layer that have stayed in the centrifugal separator 20 is released. Accompanied with the release of the platelets, the turbidity value of the liquid passing through the turbidity sensor 14 becomes high. At a time point when the voltage output of the sensor drops by 0.2 V, the third flow path shutter means 83 is closed and the fourth flow path shutter means 84 is opened. Thus the platelet-rich plasma released from the centrifugal separator 20 is collected in the platelet collecting bag 26. The voltage output from the turbidity sensor 14 is converted into the platelet concentration by the controller 13 to calculate the platelet concentration in the platelet collecting bag 26 during the platelet collecting operation. The platelet concentration in the platelet collecting bag 26 drops after reaching a maximum value. At a time point when it is detected that the maximum concentration is reached, the platelet collecting step is completed and the process proceeds to the buffy coat collecting step.

Upon completion of the platelet collecting step, the buffy coat collecting step is executed. In this step, the controller 13 closes the fourth flow path shutter means 84 and opens the fifth flow path shutter means 85. The plasma in the plasma collecting bag 25 is fed to the centrifugal separator 20 by the blood pump 11. At the same time, the liquid that has been released from the centrifugal separator 20 (the buffy coat layer portion that has flowed out) flows into the buffy coat collecting bag 27. In the buffy coat collecting step, the final rate of the blood pump in the platelet collecting step is maintained, and the rotational speed of the centrifugal separator is decreased to 4600 rpm. As a result, the buffy coat is released from the centrifugal separator 20 and collected in the buffy coat collecting bag 27. At a time point when the amount of the collected buffy coat reaches the value calculated based on the hematocrit value of the donor and the amount of platelet supplied from the donor, the blood pump 11 is stopped and all the valves are closed. Thus the centrifugal separator 20 stops rotating to complete the buffy coat collecting step.

Then, the blood returning step is executed for returning the blood in the centrifugal separator 20. The controller 13 rotates the blood pump 11 in reverse direction, opens the first flow path shutter means 81, and returns the red cell layer remaining in the centrifugal separator 20 to the donor through the first line 21.

Thus, the first (initial) platelet collecting operation is completed.

Then, the process proceeds to the second platelet collecting operation as shown in FIG. 7.

First, referring to FIG. 7, the buffy coat returning step is executed, in which the buffy coat collected in the first platelet collecting step is returned to the centrifugal separator 20 prior to the next blood-collection step. Once the process proceeds to the buffy coat returning step, the controller 13 rotates the centrifugal separator 20 at a predetermined rotational speed (say, 4800 rpm), opens the fifth flow path shutter means 85 and the fourth flow path shutter means 84, and starts the blood pump 11 at a predetermined rate (default value: 100 ml/min). The buffy coat contained in the buffy coat collecting bag 27 is fed through the fifth flow path shutter means 85 to the centrifugal separator 20. The air in the centrifugal separator 20 is sent through the second line 22 and the fourth flow path shutter means 84 to the platelet collecting bag 26. After rotating the blood pump 11 to collect the set amount of the buffy coat, the buffy coat returning step is completed.

Figure 8:
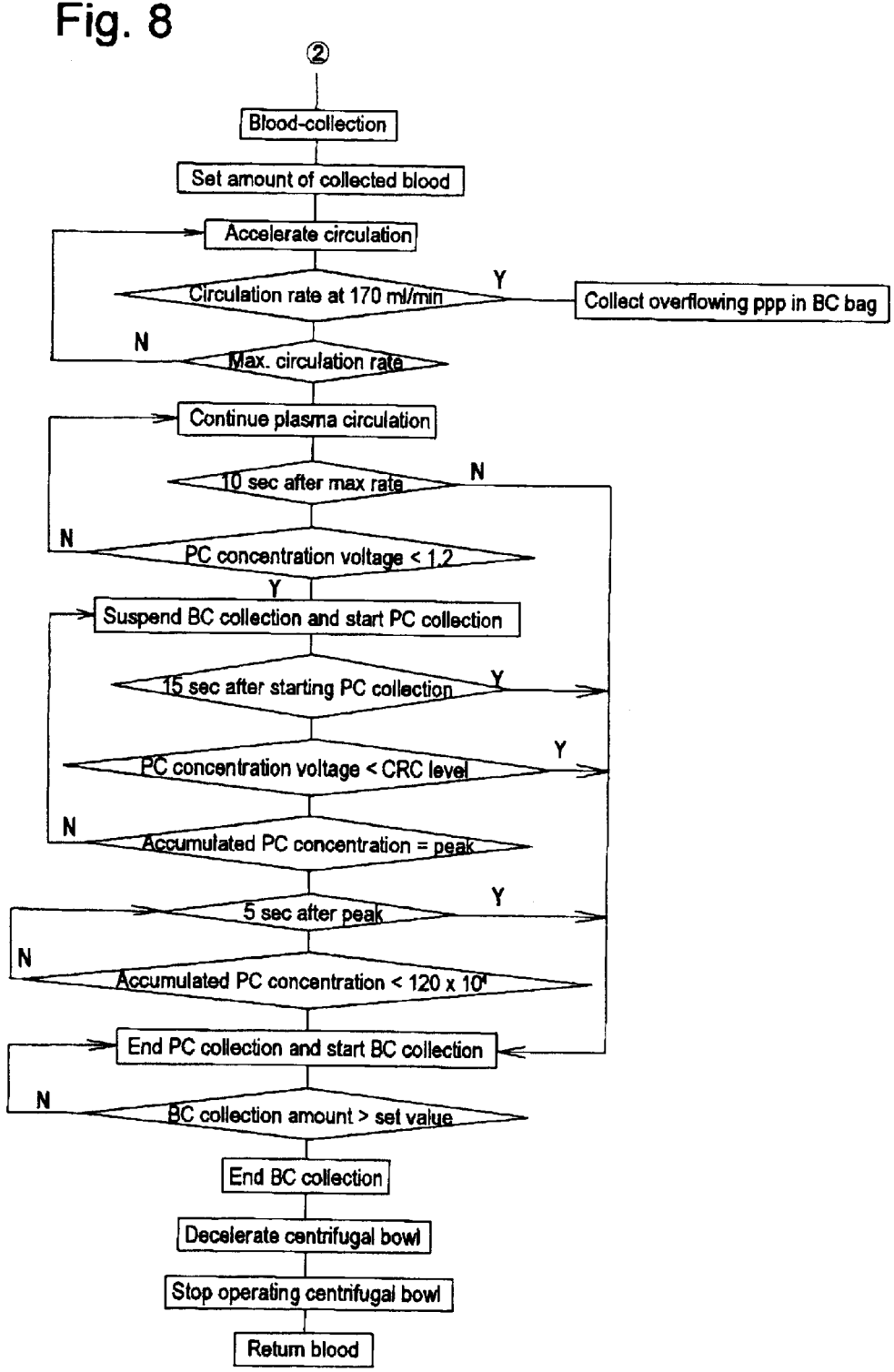
FIG. 8 is a flowchart representing the operation of a blood component collecting apparatus according to the invention.

The process proceeds to the program referred to as ② shown in FIG. 8 after completion of the first plasma collecting step, the first plasma circulation step, the second plasma collecting step, the second plasma circulation step, the third plasma collecting step, the third plasma circulation step, the fourth plasma collecting step, the fourth plasma circulation step, the fifth plasma collecting step and the fifth plasma circulation step, followed by the blood-collection step for boundary adjustment, the platelet collecting step, the buffy coat collecting step and the blood returning step to complete the second platelet collecting operation.

Now, explanation will be given with respect to the last platelet collecting operation as shown in FIG. 9. In this embodiment, the third operation is assumed to be the last one. However, the fourth or subsequent platelet collecting operation may be the last one as far as the equal effects can be obtained. Each of these platelet collecting operations except the last one is identical to the second platelet collecting operation (FIGS. 7 and 8).

First, as shown in FIG. 9, the buffy coat returning step is executed. In this step, the buffy coat collected by the second platelet collecting operation is returned into the centrifugal separator 20 prior to the next blood-collection step.

When the process proceeds to the buffy coat returning step, the controller 13 rotates the centrifugal separator 20 at a predetermined rotational speed (say 4800 rpm), opens the fifth flow path shutter means 85 and the fourth flow path shutter means 84, and activates the blood pump 11 at a predetermined rate (default value: 100 ml/min). The buffy coat contained in the buffy coat collecting bag 27 is passed through the fifth flow path shutter means 85 and supplied to the centrifugal separator 20. The air in the centrifugal separator 20 is sent to the platelet collecting bag 26 through the second line 22 and the fourth flow path shutter means 84. After rotation of the blood pump 11 to collect the set amount of buffy coat, the buffy coat returning step is completed.

Then, the first plasma collecting step is executed in which the first and second liquid supply pumps 11, 12 are started to collect the blood added anticoagulant, and the centrifugal separator drive unit 10 is activated to collect a first predetermined amount of plasma obtained from the blood into the plasma collecting bag 25.

Upon start of the first blood-collection, the first liquid supply pump 11 starts blood-collection at a predetermined rate (say, 60 ml/min). At the same time, the second pump constituting an anticoagulant pump supplies an anticoagulant (such as the ACD-A solution) at a predetermined rate (say, 1/10 of the blood pump rate). The blood supplied from the donor is mixed with the ACD solution, flows through the first line 21, the chamber and the first flow path shutter means 81 and into the centrifugal separator 20. In this process, the sixth flow path shutter means 86, the fifth flow path shutter means 85, the second flow path shutter means 82, the third flow path shutter means 83 and the seventh flow path shutter means 87 are closed. Meanwhile the first flow path shutter means 81 and the fifth flow path shutter means 85 are opened. When the blood added ACD is supplied to the centrifugal separator 20, the sterilized air that has already been admitted into the centrifugal separator 20 flows through a line sensor and the fifth flow path shutter means 85 into the buffy coat collecting bag 27. Simultaneously with the start of the blood-collection step, the centrifugal separator 20 starts rotating at a predetermined speed (say, 4800 rpm). The centrifugal separator 20 is supplied with the ACD-added blood during the rotation, such that the blood is centrifugally separated in the separator into, from the inside thereof, a plasma layer, a buffy coat layer (BC layer) and a red cell layer. When (about 270 ml of) the ACD-added blood exceeding the capacity of the centrifugal separator is supplied, the centrifugal separator 20 is filled with the blood, and the plasma overflows through the outlet of the centrifugal separator 20. The turbidity sensor 14 mounted on the second line 22 connected to the outlet of the centrifugal separator 20 detects that the fluid flowing through the line has changed from air to plasma. In response to the detection signal of the turbidity sensor 14, the controller 13 closes the fifth flow path shutter means 85 and opens the third flow path shutter means 83 to collect the plasma in the plasma collecting bag 25. The weight of the plasma collecting bag 25 is preliminarily measured by the weight sensor 16 and the weight measurement signal is applied to the controller 13. As a result, when the weight of the plasma collected in the plasma collecting bag 25 increases to a predetermined amount (say, 20 g), the controller 13 closes the first flow path shutter means 81, opens the second flow path shutter means 82, and proceeds to the first plasma circulation step.

Figure 10:
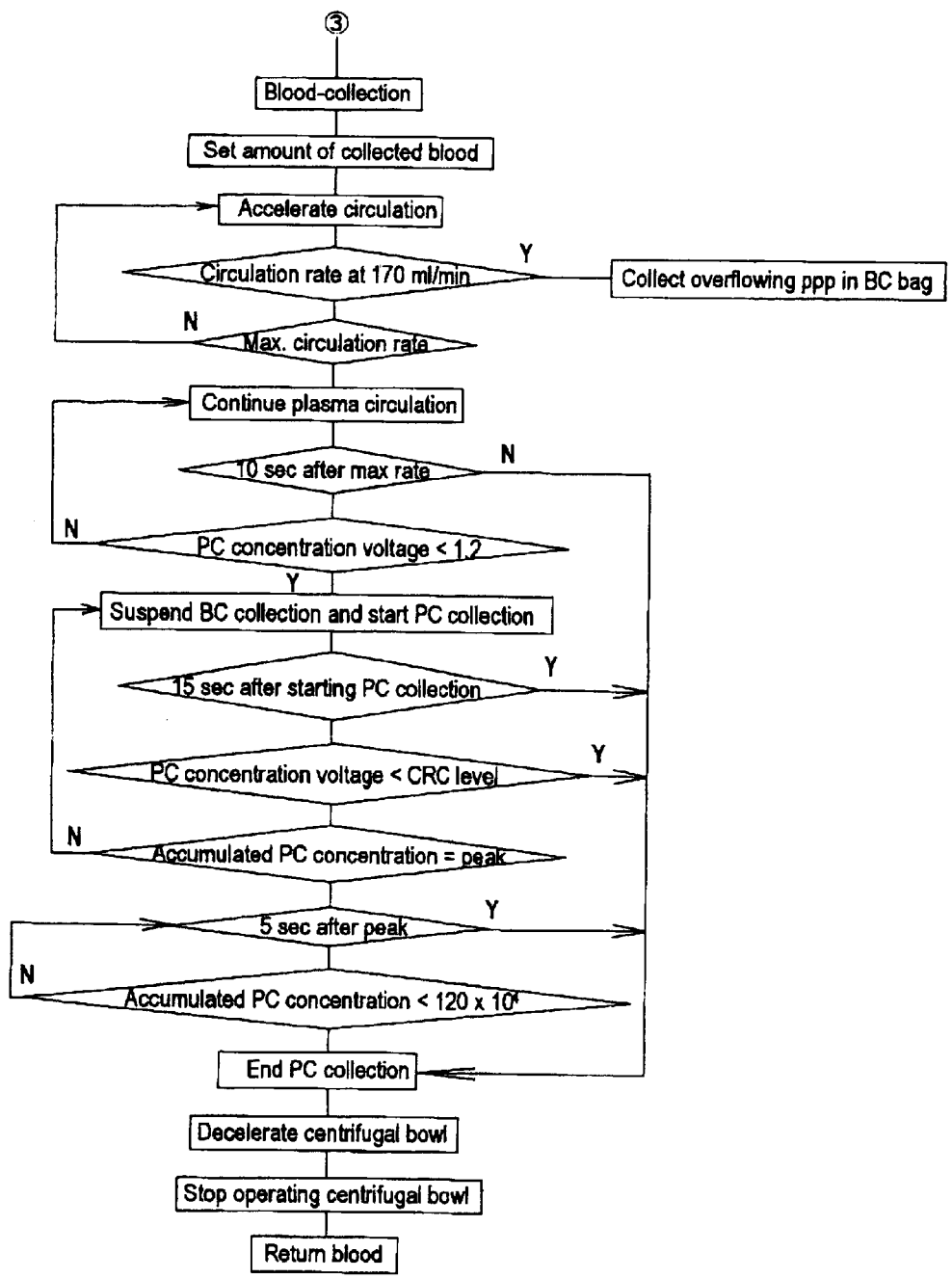
FIG. 10 is a flowchart representing the operation of a blood component collecting apparatus according to the invention.

The process then proceeds to the program referred to as ③ in FIG. 10 after the above-mentioned first plasma circulation step, the second plasma collecting step, the second plasma circulation step, the third plasma collecting step, the third plasma circulation step, the fourth plasma collecting step, the fourth plasma circulation step, the fifth plasma collecting step and the fifth plasma circulation step, followed by the blood-collection step for boundary adjustment, the platelet collecting step and the blood returning step, thus completing the last platelet collecting operation. The difference between the last and the second platelet collecting operations is that different bags are used for admitting the air in the first plasma circulation step, and the blood is returned without executing the buffy coat collecting step in the last platelet collecting operation.

It is known that in a particle suspension, the apparent viscosity of a particle suspension increases accompanied with the increase in the particle concentration. The increased viscosity reduces the difference in sedimentation velocity between particles having different specific gravity or specific size. When this fact is applied to the platelet collecting step, it follows that an increased viscosity of the particle suspension in the centrifugal separator 20 increases the probability that the white cells having higher specific gravity or specific size than that of the platelets flow out together with the platelets. During the blood-collection, the centrifugal separator 20 is rotating and the centrifugal force is constantly applied to the blood components in the centrifugal separator 20. Each blood component in the centrifugal separator 20, therefore, is progressively concentrated by the centrifugal force. As viewed from outside of the separator, therefore, as shown in FIG. 3, the blood is separated into a red cell layer, a buffy coat layer and a plasma layer. The size of particles in each layer is sequentially reduced along the direction from the outside to inside.

A plurality of what is called cake layers are formed in the centrifugal separator 20. These cake layers are steadily compressed. The newly incoming whole blood flows from the cake layer formed by the outermost cells, which are trapped in the cake layer. Meanwhile the other components are passed to the buffy coat layer and the plasma layer. In the case where the cell cake layers and the buffy coat cake layer are excessively compressed, however, the gap between fine particles in each layer is reduced. This often leads to the phenomenon where platelets are trapped in the cell cake layer or the buffy coat cake layer. The collecting efficiency of the platelets is, thus, expected to be deteriorated.

According to this invention, however, the plasma collecting step is divided into a plurality of steps and therefore the time length of each plasma collecting step can be shortened. The cake layers, therefore, are compressed more slowly. In addition, since a plurality of plasma circulation steps are provided, only the plasma components free of cells enter the centrifugal separator 20 and pass through the cell cake layer and the buffy coat cake layer within a short time. The cell cake layer and the buffy coat cake layer are thus expanded, and it is expected that the compression, if any, of the cake layers is eliminated. Consequently, the excessive compression of the cell cake layer and the buffy coat cake layer is suppressed, so that less platelets are considered to be trapped in the cell cake layer or the buffy coat cake layer.

EXAMPLES

An apparatus having a circuit configuration as shown in FIG. 4 provided with two pumps including an ACD pump and a blood pump 11 was fabricated, and the platelet collecting performance was compared between the two pumps. A comparison test was conducted on the same donor at an interval of two weeks or longer. An evaluated operation flow was compared as below (n=2 examples). The number of platelets and the number of white cells of the concentrated plasma containing platelets thus obtained was measured by Sysmex (R)NE-6000. The lower limit of WBC measurement for Sysmex is $0.1 \times 10^2$[cells/muL]. For the samples with WBC lower than the lower limit of measurement, therefore, the Nageotte [1:9] method was used for the measurement. In this example, 40 ml of the platelet was collected.

Example 1

The platelet collecting operation was conducted three times using the aforementioned method. The blood-collection rate was 60 ml/min, a first circulation after the total amount of plasma has reached 20 g was conducted under the conditions of 200 ml/min for 30 seconds, a second circulation after the total amount of plasma has reached 50 g was conducted at the rate of 120 ml/min for 30 seconds, a third circulation after the total amount of plasma has reached 80 g was conducted at the rate of 120 ml/min for 30 seconds, a fourth circulation after detection of a buffy coat layer by an optical sensor was conducted at the rate of 120 ml/min for 30 seconds. The platelets were collected under conditions of the acceleration rate of 10 ml/min/sec and the rate of 200 ml/min up to a predetermined concentration, and the buffy coat was collected at the rate of 205 ml/min up to 40 ml. In the second and third platelet collecting operations, the buffy coat was returned to the centrifugal separator prior to the blood-collection. In the third platelet collecting operation, no buffy coat was collected.

Comparative Example 1

The same apparatus as that used in the above-mentioned embodiment was employed. The platelet collecting operation was performed three times, each of which was conducted under the following conditions. Specifically, the blood-collection rate was set to 60 ml/min, and after detection of the buffy coat layer by the optical sensor, the first circulation was conducted at the rate of 120 ml/min for 3 seconds and the second circulation was conducted at the rate of 75 ml/min for 27 seconds. The platelets were collected at the acceleration rate of 8 ml/min/sec up to 50 % of the maximum platelet concentration.

The platelet concentration and the white cell concentration of the plasma with concentrated platelets thus collected in the embodiment and the reference are as follows:

TABLE 1

| | Platelet concentration [cells/muL] | |
| --- | --- | --- |
| | Sample 1 | Sample 2 |
| Example | $160.1 \times 10^4$ | $128.0 \times 10^4$ |
| Comparison Ex. | $130.1 \times 10^4$ | $123.0 \times 10^4$ |

TABLE 2

| | White cell concentration [cells/muL] | |
| --- | --- | --- |
| | Sample 1 | Sample 2 |
| Example | $0.4 \times 10^1$ | $0.4 \times 10^2$ |
| Comparison Ex. | $0.6 \times 10^2$ | $0.9 \times 10^2$ |

The blood component collecting apparatus according to this invention is provided with only two pumps, which can be reduced in size. The blood-collection is temporarily suspended in a given platelet collecting operation and the plasma recirculation step for recirculating the collected plasma in the centrifugal separator is executed at least twice. Therefore, the cell layer and the buffy coat layer are prevented from being excessively compressed in the centrifugal separator. It is therefore possible to produce a platelet-contained liquid (the plasma containing concentrated platelets) with a lesser amount of white cells mixed in and exhibiting high platelet collecting efficiency.

Further, the blood component collecting circuit including a cassette housing according to the invention can be readily mounted on a blood component collecting apparatus, leading to quick preparatory work. Also, the blood component collecting circuit can be effectively used for the blood component collecting apparatus which executes the above-mentioned plasma recirculation step.

An another blood component collection apparatus according to the present invention will be described with reference to embodiments shown in the accompanying drawings.

A blood component collection apparatus 1 according to the present invention has a blood component collection circuit 2 including a centrifugal separator 20 having a rotor 142, an internal blood storage space and an inlet and an outlet both communicating with the blood storage space and centrifugally separating blood introduced into the internal blood storage space through the inlet by a rotation of the rotor 142 into components; a first line 21 for connecting a connector of a blood collection needle 29 or a blood pool and the inlet of the centrifugal separator 20 with each other; a second line 22 connected to the outlet of the centrifugal separator 20; a third line 23 connected to the first line 21 and injecting an anticoagulant to the blood; a plasma collection bag 25 having a first tube 25a connected with the first line 21 and a second tube 25b connected with the second line 22; and a platelet collection bag 26 connected with the second line 22.

Referring to FIG. 4 in particular, the blood component collection apparatus 1 has a centrifugal separator drive unit 10 for rotating the rotor 142 of the centrifugal separator 20; a first liquid supply pump 11 to be used individually for the first line 21; a second liquid supply pump 12 to be used individually for the third line 23; a plurality of flow path shutter means 81, 82, 83, 84, 85, 86, and 87 for opening/closing flow paths of the blood component collection circuit 2, and a controller 13 for controlling the centrifugal separator drive unit 10, the first liquid supply pump 11, the second liquid supply pump 12, and a plurality of the flow path shutter means 81, 82, 83, 84, 85, 86, and 87.

The blood component collection circuit 2 will be described in detail below.

The blood component collection circuit 2 is used to collect a blood component, more specifically, platelets. The blood component collection circuit 2 includes a blood collector such as a blood collection needle 29 or a connector (connector of blood collector) connected with the blood collection needle 29 or with a blood collector having a blood pool connector; the first line 21 (blood collection/blood return line) connecting the blood collection needle 29 or the connector of the blood collector and the inlet of the centrifugal separator 20 with each other and having a first pump tube 21g; the second line 22 for connecting the outlet of the centrifugal separator 20 and the first line 21 with each other; the third line (anticoagulant injection line) 23 connected wit a position, of the first line 21, near the blood collection needle 29 and having a second pump tube 23a; a plasma collection bag 25 having the first tube 25a connected with a position, of the first line 21, located between the blood collection needle 29 and the first pump tube 21g and the second tube 25b connected with the second line 22; the platelet collection bag 26 having a third tube 26a connected with the second line 22; a buffy coat collection bag 27 having a fourth tube 27a connected with the second line 22; and a fourth line 24 connected with the second line 22 and injecting liquid (physiological salt solution). Instead of the blood collection needle 29, the blood component collection circuit 2 may employ a connector (such as a metal or plastic needle) to be connected with a blood pool such as a blood bag.

A known metal needle is used as the blood collection needle 29. The first line 21 includes a blood collection needle-side part 21a with which the blood collection needle 29 is connected and a centrifugal separator-side part 21b with which the inlet of the centrifugal separator 20 is connected. The blood collection needle-side part 21a is formed of a plurality of soft plastic tubes. The blood collection needle-side part 21a has the following elements arranged as viewed from the side of the blood collection needle 29: a branching connector 21c for connecting the blood collection needle-side part 21a and the third line 23 with each other; a chamber 21d for removing bubbles and micro-aggregates; a branching connector 21e for connecting the blood collection needle-side part 21a and the second line 22 with each other; and a branching connector 21f for connecting the first line 21 and the first tube 25a of the plasma collection bag 25 with each other. The chamber 21d is connected to an air-permeable and germ-blocking filter 21i. The centrifugal separator-side part 21b is connected with the branching connector 21f connected with the first tube 25a and has the first pump tube 21g formed in the vicinity of the branching connector 21f.

The second line 22 connecting the outlet of the centrifugal separator 20 and the first line 21 with each other has an end thereof connected to the outlet of the centrifugal separator 20 and the other end thereof connected to the branching connector 21e for connecting the blood collection needle-side part 21a and the second line 22 with each other. The second line 22 has the following elements arranged as viewed from the side of the centrifugal separator 20: a branching connector 22a for connecting the second line 22 with the second tube 25b of the plasma collection bag 25 and with the third tube 26a of the platelet collection bag 26; a branching connector 22b for connecting the second line 22 with the fourth line 24; a branching connector 22c for connecting the second line 22 with a tube having a bubble-removing filter 22f; and a branching connector 22d for connecting the second line 22 with the fourth tube 27a connected with the buffy coat collection bag 27.

The third line 23 is connected with the branching connector 21c having an end thereof connected to the first line 21. The third line 23 has the following elements arranged as viewed from the connector 21c: a pump tube 23a; a foreign matter removing filter 23b; a bubble removing chamber 23c; and an anticoagulant container-connecting needle 23d.

One end of the fourth line 24 is connected with the branching connector 22b for connecting the second line 22 and the fourth line 24 with each other. The fourth line 24 has the following elements arranged as viewed from the connector 22b: a foreign matter-removing filter 24a and a physiological salt solution container connecting needle 24b.

The plasma collection bag 25 includes the first tube 25a connected with the branching connector 21f located between the blood collection needle 29 and the pump tube $^{21}g$ of the first line 21; and the second tube 25b connected with the branching connector 22a of the second line 22. The platelet collection bag 26 includes the third tube 26a connected with the branching connector 22a of the second line 22. The buffy coat collection bag 27 includes the fourth tube 27a connected with the branching connector 22d of the second line 22.

The tubes and the pump tubes used to form the first to fourth lines and the tubes connected to the bags as described above are composed of such materials as polyvinyl chloride, polyethylene, polypropylene, polyester such as PET or PBT, ethylene-vinyl acetate copolymer, polyurethane, polyester elastomer, thermoplastic elastomer such as styrene-butadiene-styrene copolymer. Of all these component materials, polyvinyl chloride is the most favorable. If all the tubes are made of polyvinyl chloride, they have sufficient flexibility and plasticity for easy handling. Also, this material is suitably used to cope with clogging caused by a clamp and the like. Component materials similar to these tube materials can also be used to form the branching connectors. The pump tubes strong enough to bear a pressure applied thereto by roller pumps 11, 12 are used in the embodiment.

Each of the plasma collection bag 25, the platelet collection bag 26, and the buffy coat collection bag 27 is composed of layers of flexible plastic sheets having the peripheral edges thereof fusion bonded (thermally or with high frequencies) or adhered. Soft polyvinyl chloride is the most favorable material for forming the bags 25, 26, and 27. Plasticizers used for the soft polyvinyl chloride include, for example, di-(ethylhexyl) phthalate (DEHP), di-(n-decyl) phthalate (DnDP) and the like. The content of these plasticizers preferably ranges from approximately 30 to 70 parts by weight for 100 parts by weight of the polyvinyl chloride.

Other sheet materials that can be used to form the bags 25, 26, and 27 are polyolefin, namely, a polymer formed by polymerizing or copolymerizing an olefin or di-olefin of ethylene, propylene, butadiene, isoprene or the like. More specifically, polyethylene, polypropylene, ethylene-vinyl acetate copolymer (EVA), polymer blend of EVA and various thermoplastic elastomers, etc. or an arbitrary combination thereof can be used. Still other applicable materials include polyester such as polyethylene terephthalate (PET), polybutylene terephthalate (PBT), poly-1,4-cyclohexanedimethyl terephthalate (PCHT) and polyvinylidene chloride.

It is preferable to use a sheet material superior in gas permeability for the platelet collection bag 26 for assuring an improved platelet shelf life. Such sheet materials include the above-mentioned polyolefin or DnDP plasticized polyvinyl chloride, etc. Alternatively, comparatively thin (for example, about 0.1 to 0.5 mm thick, or especially, about 0.1 to 0.3 mm thick) materials can be preferably used. The platelet collection bag can be preliminarily filled with a platelet preservation liquid such as physiological salt solution, GAC, PAS, PSM-1.

Essential portions of the blood component collection circuit 2 are housed in a cassette, as shown in FIG. 2. The blood component collection circuit 2 includes a cassette housing 28 partially accommodating or partially holding all the lines (first, second, third, and fourth lines) and all the tubes (first, second, third, and fourth tubes). In other words, they are partially fixed to the cassette housing 28. The cassette housing 28 holds both ends of the first pump tube 21g and the second pump tube 23a fixed thereto. The pump tubes 21g, 23a project from the cassette housing 28 in the shape of a loop in correspondence to that of the roller pumps 11, 12, respectively. Therefore, the first and the second pump tubes 21g, 23a can be readily mounted on the roller pumps 11, 12, respectively.

Further, the cassette housing 28 has a plurality of openings located therein. Specifically, located in the cassette housing 28 are a first opening 91 that exposes the portion of the first line 21 between the blood collection needle 29 and the pump tube 21g and can be penetrated by the first flow path shutter means 81 of the blood component collection apparatus 1; a second opening 92 that exposes the first tube 25a of the plasma collection bag 25 and can be penetrated by the second flow path shutter means 82 of the blood component collection apparatus 1; a third opening 93 that exposes the second tube 25b of the plasma collection bag 25 and can be penetrated by the third flow path shutter means 83 of the blood component collection apparatus 1; a fourth opening 94 that exposes the third tube of the platelet collection bag 26 and can be penetrated by the fourth flow path shutter means 84 of the blood component collection apparatus 1; a fifth opening 95 that exposes the portion (upstream side) of the second line 22 located between the centrifugal separator (connector 22c) 20 and the connector 22d for connecting the fourth tube 27a of the buffy coat collection bag 27 and the second line 22 with each other and can be penetrated by the fifth flow path shutter means 85 of the blood component collection apparatus 1; a sixth opening 96 that exposes the portion of the second line 22 located between the connector 21e for connecting the first line 21 and the second line 22 with each other and the connector 22d for connecting the fourth tube 27a of the buffy coat collection bag 27 and the second line 22 with each other and can be penetrated by the sixth flow path shutter means 86 of the blood component collection apparatus 1; and a seventh opening 97 that exposes the fourth line 24 and can be penetrated by the seventh flow path shutter means 87 of the blood component collection apparatus 1.

The above-mentioned branching connectors are fixed to the inner surface of the cassette housing 28. In the vicinity of the side surface of the cassette housing 28, there are provided reinforcing tubes for holding the lines and tubes projecting from the side surface of the cassette housing 28 and preventing them from being bent. The cassette housing 28 is box-shaped and contains parts indicated with dashed lines of FIG. 2. The cassette housing 28 is formed of synthetic resin having a certain degree of rigidity.

The blood component collection apparatus 1 includes a cassette housing-mounting portion (not shown). When the cassette housing 28 is mounted on the cassette housing-mounting portion of the blood component collection apparatus 1, the lines and the tubes exposed from the openings of the cassette housing 28 are automatically mounted on the corresponding flow path shutter means, respectively. Thus, the blood component collection circuit 2 can be easily mounted on the blood component collection apparatus 1 and rapid preparations for collecting blood components can be accomplished. The blood component collection apparatus 1 has two pumps proximately to the cassette housing-mounting portion. Thus, the pump tubes exposed from the cassette housing 28 can be easily mounted on the pumps.

The centrifugal separator 20, a so-called centrifugal bowl, is mounted on the blood component collection circuit 2 to separate blood into components by a centrifugal force. As shown in FIG. 3, the centrifugal separator 20 includes a tubular member 141 extending vertically and having an inlet 143 formed at the upper end thereof and a hollow rotor. 142 sealed to prevent liquid from flowing thereinto from an upper portion 145 of the centrifugal separator 20 and rotating around the tubular member 141. The rotor 142 has a flow path (blood storage space) formed along the bottom and the inner peripheral surface thereof. An outlet 144 is so formed as to communicate with the upper portion of the flow path. The volume of the rotor 142 ranges from 100 to 350 ml.

The rotor 142 is rotated under predetermined centrifugal conditions (rotational speed and rotation time) set by the rotor (centrifugal separator) drive unit 10 of the blood component collection apparatus 1. Based on the centrifugal conditions, patterns (for example, the number of blood components to be separated) of blood separation to be made in the rotor 142 can be set. As shown in FIG. 3, according to the embodiment, the centrifugal conditions are set such that the blood is separated into a plasma layer (inner layer) 131, a buffy coat layer (intermediate layer) 132, and a red cell layer (outer layer) 133 laminated in the flow path of the rotor 142.

Referring to FIG. 4, the blood component collection apparatus 1 according to the present invention will be described.

The blood component collection apparatus 1 includes the centrifugal separator drive unit 10 for rotating the rotor 142 of the centrifugal separator 20; the first liquid supply pump 11 to be used individually for the first line 21; the second liquid supply pump 12 to be used individually for the third line 23; a plurality of the flow path shutter means 81, 82, 83, 84, 85, 86, and 87 for opening/closing the flow paths of the blood component collection circuit 2; and the controller 13 for controlling the centrifugal separator drive unit 10, the first liquid supply pump 11, the second liquid supply pump 12, and the flow path shutter means 81, 82, 83, 84, 85, 86, and 87. The blood component collection apparatus 1 further includes a turbidity sensor 14 mounted on the portion, of the second line 22, located between the centrifugal separator 20 and the connector 22a for connecting the second tube 25b with the second line 22; an optical sensor 15 mounted above the centrifugal separator 20; and a weight sensor 16 for detecting the weight of the plasma collection bag 25.

The controller 13 includes two pump controllers (not shown) one of which is used individually for the first liquid supply pump 11 and the other of which is used individually for the second liquid supply pump 12. A control mechanism of the controller 13 is electrically connected to the first liquid supply pump 11 through the one pump controller and to the second liquid supply pump 12 through the other pump controller. A drive controller of the centrifugal separator drive unit 10 is electrically connected with the controller 13. The flow path shutter means 81, 82, 83, 84, 85, 86, and 87 are all connected with the controller 13 for controlling the opening/closing thereof. The turbidity sensor 14, the optical sensor 15 installed above the centrifugal separator 20, and the weight sensor 16 for detecting the weight of the plasma collection bag 25 are electrically connected with the controller 13 to which signals are transmitted from these sensors. The control mechanism of the controller 13 is constructed of a microcomputer. Detection signals outputted from the weight sensor 16, the optical sensor 15, and the turbidity sensor 14 are applied to the controller 13. The controller 13 controls the start and stop of the rotation and rotational direction (forward/backward) of each pump, based on the signals applied thereto from the turbidity sensor 14, the optical sensor 15, and the weight sensor 16. The controller 13 also controls the opening/closing of the flow path shutter means 81, 82, 83, 84, 85, 86, and 87 and the centrifugal separator drive unit 10.

The first flow path shutter means 81 is used to open/close the portion of the first line 21 located between the blood collection needle 29 and the pump tube 21g. The second flow path shutter means 82 is used to open/close the first tube 25a of the plasma collection bag 25. The third flow path shutter means 83 is used to open/close the second tube 25b of the plasma collection bag 25. The fourth flow path shutter means 84 is used to open/close the third tube 26a of the platelet collection bag 26. The fifth flow path shutter means 85 is used to open/dose the portion of the second line 22 located between the centrifugal separator 20 and the connector 22d for connecting the second line 22 with the fourth tube 27a of the buffy coat collection bag 27. The sixth flow path shutter means 86 is used to open/dose the portion of the second line 22 located downstream from the connector 21e for connecting the first line 21 and the second line 22 with each other to the connector 22d for connecting the fourth tube 27a of the buffy coat collection bag 27 and the second line 22 with each other. The seventh flow path shutter means 87 is used to open/dose the fourth line 24. Each of the flow path shutter means 81 through 87 has an insertion portion on which the lines or the tubes are installed. The insertion portion has a clamp to be operated by a drive source such as a solenoid, an electric motor, and a hydraulic or pneumatic cylinder. An electromagnetic clamp to be operated by the solenoid is preferable. The clamp of each of the flow path shutter means 81 through 87 is operated based on a signal transmitted thereto from the controller 13.

As shown in FIG. 3, the centrifugal separator drive unit 10 includes a rotor drive unit housing 151 accommodating the centrifugal separator 20, a pedestal 152, a motor 153 constituting the drive source, and a disk-shaped rest 155 for holding the centrifugal separator 20. The housing 151 is fixedly mounted on the pedestal 152. The motor 153 is fixed to the lower surface of the housing 151 with a bolt 156 via a spacer 157. The upper end of the rotary shaft 154 of the motor 153 is fitted in the rest 155 such that the rest 155 rotates coaxially and integrally with the rotational shaft 154. The upper portion of the rest 155 has a recess formed therein into which the bottom of the rotor 142 is fitted. The upper portion 145 of the centrifugal separator 20 is fixed to the housing 151 with a fixing member not shown. Once the motor 153 for the rotor drive unit 10 is started, the rest 155 and the rotor 142 fixed thereto are rotated at a rotational speed ranging from 3000 to 6000 rpm.

The rotor drive unit housing 151 has the optical sensor 15 fixedly mounted on an inner wall thereof with a mounting member 158. The optical sensor 15 optically detects the boundaries between separated blood components (for example, the boundary B between the plasma layer 131 and the buffy coat layer 132 and the boundary between the buffy coat layer 132 and the red cell layer 133) in the centrifugal separator 20. The optical sensor 15 is of a type capable of vertically scanning the peripheral surface of the rotor 142. The optical sensor 15 includes a light source for emitting a light beam to a shoulder portion of the centrifugal separator 20 and a light-receiving part for receiving a light-beam reflected by the centrifugal separator 20 and returned therefrom. That is, a light emitting element such as an LED or laser and a light-receiving element are arrayed in a row. A light beam emitted by the light emitting element and reflected by a blood component is received by the light-receiving element, and the amount of the received light is photoelectrically converted. Because the intensity of the reflected light varies depending on the separated blood component (for example, the boundary B between the plasma layer 131 and the buffy coat layer 132), a position of the light-receiving element at which the amount of received light has changed is detected as the corresponding position of the boundary B. More specifically, the arrival of the buffy coat layer at a light passage portion is detected, based on the difference between the amount of received light at the time when the light passage portion of the centrifugal separator 20 is filled with a transparent liquid (plasma or water) and the amount of received light at the time when the light passage portion thereof is filled with the buffy coat layer. The detection position of the buffy coat layer is adjusted by changing a light passage position in the centrifugal separator 20. Normally, the detection of the light passage position is unchangeably set.

The turbidity sensor 14 detects the turbidity of a fluid flowing through the second line 22 and outputs a voltage corresponding to the detected turbidity. Specifically, the turbidity sensor 14 outputs a low voltage when the turbidity is high, while it outputs a high voltage when the turbidity is low.

As each of the first liquid supply pump 11 on which the pump tube 21g of the first line 21 is mounted and the second liquid supply pump 12 on which the pump tube 23a of the third line 23 is mounted, a roller pump or a peristaltic pump which is kept out of contact with the blood is preferably used. A pump that can supply the blood in either direction is used as the first liquid supply pump 11 (blood pump). A roller pump capable of rotating forward/backward is used.

The controller 13 executes a plasma collection/constant-speed circulation step and then, a plasma collection/acceleration circulation step. More specifically, the plasma collection/constant-speed circulation step includes a first plasma collection step of collecting anticoagulant-added blood by starting the first and second liquid supply pumps 11, 12 and collecting a first predetermined amount of plasma into the plasma collection bag 25 by activating the centrifugal separator drive unit 10. The plasma collection/constant-speed circulation step also includes a constant-speed plasma circulation step of temporarily suspending the blood collection and circulating the plasma contained in the plasma collection bag 25 to the centrifugal separator 20 at a constant speed by activating the centrifugal separator drive unit 10. The plasma collection/acceleration circulation step includes a second plasma collection step of collecting the anticoagulant-added blood by starting the first and second liquid supply pumps 11, 12 and collecting the plasma by activating the centrifugal separator drive unit 10 until a boundary sensor detects a predetermined position (for example, BC layer). The plasma collection/acceleration circulation step also includes an acceleration plasma circulation step of temporarily suspending the blood collection after the second plasma collection step terminates and circulating the plasma contained in the plasma collection bag 25 to the centrifugal separator 20 at an accelerated speed by activating the centrifugal separator drive unit 10. In the second plasma collection step, the boundary sensor detects the boundary between blood components. Thus, detection of the weight of the plasma bag is not executed.

The controller 13 of the blood component collection apparatus 1 according to the embodiment controls the centrifugal separator drive unit 10, the first liquid supply pump 11, the second liquid supply pump 12, and a plurality of the flow path shutter means 81 through 87 to execute the platelet collection operation including the plasma collection/constant-speed circulation step and the plasma collection/acceleration circulation step twice.

Subsequent to the termination of the execution of a platelet collection step and prior to the start of the execution of a blood return step, the controller 13 of the blood component collection apparatus 1 executes a buffy coat-collection step of flowing out the buffy coat from the centrifugal separator 20 and collecting it into the buffy coat collection bag 27 by setting a plasma circulation rate higher than a final plasma circulation rate in the platelet collection step by means of the first liquid supply pump 11. The buffy coat collection step is not limited to the above-mentioned method. As an example, the buffy coat collection step may be executed by maintaining the plasma circulation rate at the final plasma circulation rate in the platelet collection step by means of the first liquid supply pump 11 and decreasing the rotational speed of the rotor 142 of the centrifugal separator 20. As another example, the buffy coat collection step may be executed by setting the plasma circulation rate higher than the final plasma circulation rate in the platelet collection step by means of the first liquid supply pump 11 and decreasing the rotational speed of the rotor 142 of the centrifugal separator 20.

After the execution of the buffy coat collection step terminates and before the execution of the subsequent blood collection step starts, the controller 13 controls the first liquid supply pump 11 and a plurality of the flow path shutter means 81 through 87 to execute the buffy coat return step of returning the collected buffy coat to the centrifugal separator 20.

Specifically, an anticoagulant is added to the whole blood at a predetermined ratio (1/8 to 1/20, specifically, 1/10 of the whole blood). The anticoagulant-added blood is fed to the centrifugal separator 20 through the first line 21 at a predetermined rate (250 ml/min or less, preferably, 150 to 40 ml/min or less, or specifically, 60 ml/min or less). The centrifugal separator 20 is rotated at a predetermined rotational speed (3000 to 6000 rpm, or preferably, 4700 to 4800 rpm) to separate the blood into the plasma, the buffy coat, and the red cells. The plasma that has overflowed the centrifugal separator 20 is collected in the plasma collection bag 25. At a time point when a predetermined amount (10 to 150 ml, or preferably 20 to 30 ml) of the plasma is collected, the blood supply is stopped. Then, the plasma is returned to the centrifugal separator 20 through the first and second lines 21, 22 under predetermined conditions (at a rate higher than that in the blood collection, namely, 60 to 250 ml/min for 10 to 90 seconds, or specifically, 200 ml/min for 30 seconds in the first circulation). That is, a constant-speed plasma circulation is executed.

Then, the anticoagulant is added again to the whole blood at the predetermined ratio (1/8 to 1/20, specifically, 1/10 of the whole blood). The anticoagulant-added blood is fed to the centrifugal separator 20 through the first line 21 at the predetermined rate (250 ml/min or less, preferably, 150 to 40 ml/min or less, specifically, 60 ml/min or less). The centrifugal separator 20 is rotated at the predetermined rotational speed (3000 to 6000 rpm, preferably, 4700 to 4800 rpm) to separate the blood into the plasma, the buffy coat, and the red cells. When the position of the boundary of blood cells inside the centrifugal separator 20 is detected by the buffy coat boundary sensor, the blood supply is stopped. Then, the plasma is returned to the centrifugal separator 20 through the first and second lines 21, 22 under predetermined conditions (initial speed: 60 to 250 ml/min, final arrival speed (set speed) 150–250 ml/min, acceleration condition: increase of 2–10 ml/min, and circulation time period: 10–90 seconds). That is, an acceleration plasma circulation is executed.

After the whole anticoagulant-added blood is fed again under predetermined conditions (collection amount of blood: 0 to 2500/Hct% [ml], specifically, 400 to 1000/Hct% [ml]), the plasma is returned to the centrifugal separator 20 through the first and second lines 21, 22 under the predetermined conditions. The acceleration rate is increased stepwise under predetermined conditions (stepwise acceleration ranging from 0.1 to 99 ml/min/sec, or specifically, 2–10 ml/min/sec) until the platelet collection rate (60 to 250 ml/min, or actually, 200 ml/min) is attained. The platelets released from the centrifugal separator 20 are collected in the platelet collection bag 26. Then, in the blood component collection apparatus 1, the blood circulation rate (at 60 to 250 ml/min., specifically, 200 ml/min) is maintained while reducing the rotational speed of the centrifugal separator 20 (by 100 to 300 rpm, preferably by 4500 to 4600 rpm). In this way, the released buffy coat is collected and supplied to the centrifugal separator 20 prior to the start of the next blood collection cycle. The buffy coat may be collected by increasing the blood circulation rate to a predetermined one (not less than the platelet collection rate, preferably 60 to 250 ml/min., specifically, 205 ml/min.) after the platelets are collected.

The blood component collection process (first platelet collection operation) to be executed by the blood component collection apparatus 1 according to the embodiment will be described with reference to flowcharts of FIGS. 4, 11 to 16. In the embodiment, the platelet collection operation is repeated twice, and after the execution of each platelet collection step other than the last one terminates and prior to the start of the execution of the blood return step, the buffy coat collection step is executed. Prior to the start of the execution of the next blood collection step, the buffy coat return step is performed to return the buffy coat to the centrifugal separator 20.

First, the third line 23 and the blood collection needle 29 are primed with the anticoagulant and then the blood collection needle 29 is stuck on the donor.

Figure 11:
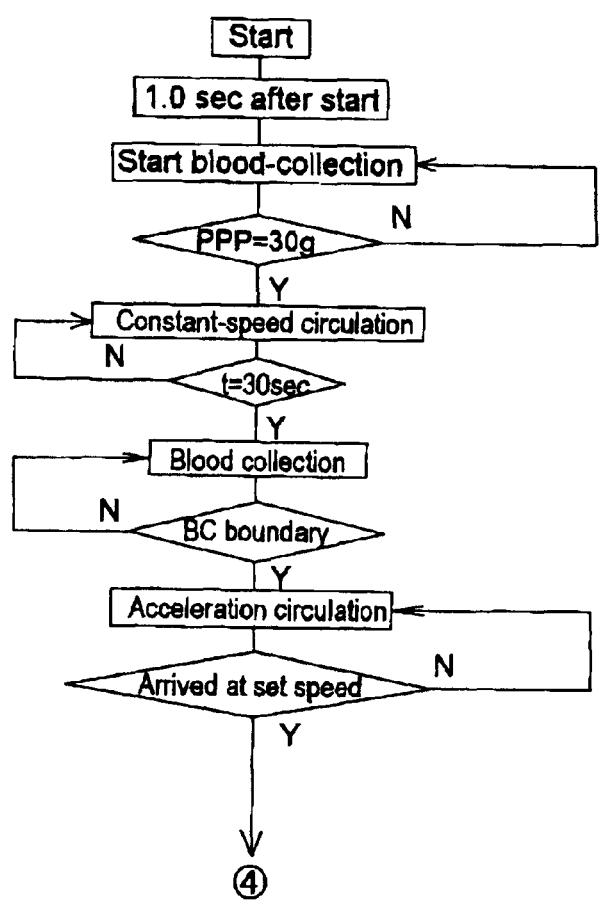
FIG. 11 is a flowchart for describing the operation of the blood component collection apparatus according to the present invention.

As shown in FIG. 11, the controller 13 executes the first plasma collection step of collecting the anticoagulant-added blood by starting the first and second liquid supply pumps 11, 12 and collecting the first predetermined amount of the plasma into the plasma collection bag 25 by activating the centrifugal separator drive unit 10.

When the first blood collection starts, the blood pump 11 is rotated at a predetermined rate (for example, 60 ml/min). At this time, a second pump constituting the anticoagulant pump supplies the anticoagulant (for example, ACD-A solution) at a predetermined rate (for example, 1/10 of the blood pump rate). The blood drawn from the donor is mixed with the ACD-A solution, flows through the first line 21, the chamber, and the first flow path shutter means 81, and flows into the centrifugal separator 20. At the above time point, the sixth flow path shutter means 86, the fifth flow path shutter means 85, the second flow path shutter means 82, the third flow path shutter means 83, and the seventh flow path shutter means 87 are closed. Meanwhile the first flow path shutter means 81 and the fourth flow path shutter means 84 are open. When the ACD-A solution-added blood is fed to the centrifugal separator 20, sterilized air that has stayed in the centrifugal separator 20 flows into the platelet collection bag 26 through the second line 22 and the flow path shutter means 84. Simultaneously with the start of the blood collection, the centrifugal separator 20 starts rotating at a predetermined speed (for example, 4800 rpm) while it is being supplied with the ACD-A solution-added blood. In the centrifugal separator 20, therefore, the blood is centrifugally separated into a plasma layer (inner layer), a buffy coat layer (BC layer, intermediate layer), and a red cell layer (outer layer). When the ACD-A solution-added blood (about 270 ml) is supplied in excess of the capacity of the centrifugal separator 20, the centrifugal separator 20 is completely filled with the blood, and the plasma overflows through the outlet of the centrifugal separator 20. The turbidity sensor 14 mounted on the second line 22 connected with the outlet of the centrifugal separator 20 detects that the fluid flowing through the second line 22 has changed from the air to the plasma. Upon receipt of the detection signal transmitted from the turbidity sensor 14, the controller 13 closes the fourth flow path shutter means 84 and opens the third flow path shutter means 83 to collect the plasma into the plasma collection bag 25. The weight of the plasma collection bag 25 is measured in advance by the weight sensor 16, and a signal indicating the measured weight is transmitted to the controller 13. Thus, when the weight of the plasma collected in the plasma collection bag 25 is increased to a predetermined amount (10 to 150 g, for example, 20 g), the controller 13 closes the first flow path shutter means 81 and opens the second flow path shutter means 82 to proceed to the constant-speed plasma circulation step.

In the constant-speed circulation step, the blood collection is temporarily suspended, and the centrifugal separator drive unit 10 is activated to circulate the plasma contained in the plasma collection bag 25 to the centrifugal separator 20 at a constant speed.

Upon start of the execution of the constant-speed circulation step, the controller 13 keeps the first flow path shutter means 81 closed and the second flow path shutter means 82 opened, stops the ACD-A pump 12, and starts the blood pump 11 at the predetermined rate (60 to 250 ml/min, for example, 200 ml/min). The plasma collected in the plasma collection bag 25 is fed to the centrifugal separator 20 rotating at 4800 rpm through the second flow path shutter means 82. At the same time, the plasma which has flowed from the centrifugal separator 20 flows into the plasma collection bag 25 through the turbidity sensor 14 and the third flow path shutter means 83. With the lapse of a predetermined length of time (10 to 90 sec, for example, 30 seconds) from the start of the constant-speed circulation step, the controller 13 closes the second flow path shutter means 82 and opens the first flow path shutter means 81 to proceed to the second plasma collection step. The first plasma circulation step is executed preferably at the flow rate of 60 ml/min or more for at least 10 seconds.

In the second plasma collection step, the first and second liquid supply pumps 11, 12 are started to collect the anticoagulant-added blood. Upon detection of the buffy coat layer in the centrifugal separator 20 because of an increase in the amount of the plasma in the platelet collection bag 26, a detection signal is transmitted from the optical sensor 15 to the controller 13. Upon receipt of the signal, the controller 13 closes the first flow path shutter means 81 and opens the second flow path shutter means 82 to proceed to the acceleration plasma circulation step.

More specifically, the first blood pump 11 is activated to collect the blood at a predetermined rate (for example, 60 ml/min). At this time, the second pump constituting the anticoagulant pump supplies the anticoagulant (for example, ACD-A solution) at a predetermined rate (for example, 1/10 of the rate of the blood pump). The blood drawn from the donor is mixed with the ACD-A solution. The ACD-A solution-added blood flows into the centrifugal separator 20 rotating at a predetermined rate (for example, 4800 rpm), and the plasma is collected in the plasma collection bag 25. Normally, upon detection of the buffy coat layer in the centrifugal separator 20 because of an increase in the amount of the plasma in the platelet collection bag 26, a detection signal is transmitted from the optical sensor 15 to the controller 13. Upon receipt of the signal, the controller 13 closes the first flow path shutter means 81 and opens the second flow path shutter means 82 to proceed to the acceleration plasma circulation step. In the second plasma collection step, the plasma is collected until the optical sensor 15 detects the buffy coat (BC boundary: boundary between plasma layer and buffy coat layer).

In the acceleration plasma circulation step, the blood collection is temporarily suspended and the centrifugal separator drive unit 10 is activated to circulate the plasma in the plasma collection bag 25 to the centrifugal separator 20. In the process, the blood pump operates at an initial rate, for example, at 60 ml/ min lower than that in the constant-speed plasma circulation step and accelerated at 6.7 ml/min for 21 seconds until a final rate reaches 200 ml/min. Upon completion of the acceleration plasma circulation step, the process proceeds to ④ of the flowchart of FIG. 12 showing a blood collection step for adjustment of boundary.

Figure 12:
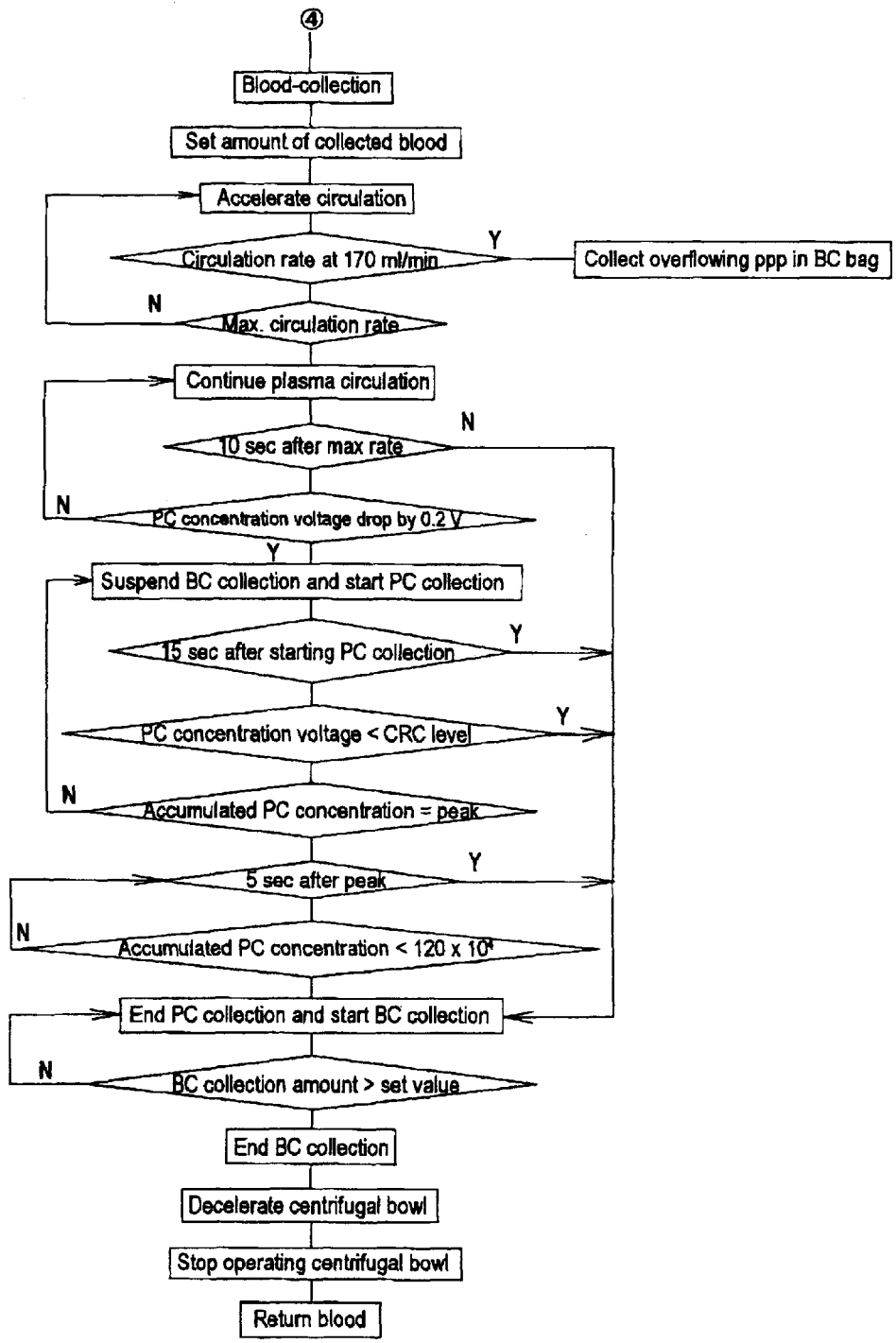
FIG. 12 is a flowchart for describing the operation of the blood component collection apparatus according to the present invention.

As shown in FIG. 12, the blood collection step for boundary adjustment can be regarded as a step of collecting a small amount of plasma. In this step, in order to keep the position of the buffy coat layer constant, irrespective of donors in the subsequent platelet collection step, the blood is collected in correspondence to a predetermined amount of red cells to be supplied. The supply amount of the red cells is defined as a value derived from dividing a collected amount of blood by the hematocrit value of the donor. Practically about 12 ml of the blood is collected. The blood collection starts by rotating the first liquid supply pump 11 at a predetermined rate (for example, 60 ml/min). At this time, the second pump constituting the anticoagulant pump also supplies the anticoagulant (such as the ACD-A solution) at a predetermined rate (for example, 1/10 of the blood pump rate). The blood collected from the donor is mixed with the ACD-A solution. The ACD-A solution-added blood flows into the centrifugal separator 20 rotating at a predetermined rate (for example, 4800 rpm), and a small amount of plasma is collected. Based on a set collection amount and a set pump rotation rate, the controller 13 computes a blood collection time, and terminates the blood collection when the computed blood collection time expires. Then the controller 13 closes the first flow path shutter means 81 and opens the second flow path shutter means 82 to proceed to the platelet collection step.

Upon termination of the acceleration plasma circulation step, the controller 13 executes the platelet collection step of flowing out platelets from the centrifugal separator 20 and collecting them into the platelet collection bag 26 by accelerating the plasma circulation rate by means of the first liquid supply pump 11. The platelet collection step is called an acceleration process. In this step, the controller 13 controls the rotational speed of the blood pump to increase it stepwise by 10 ml/min every predetermined time period (for example, every one second) from 60 ml/min to 200 ml/min. When the rotational speed of the blood pump reaches 200 ml/min, it is maintained until the platelet collection step terminates.

Upon start of the platelet collection step, the turbidity sensor 14 detects the turbidity of a liquid passing therethrough and outputs a voltage corresponding to a detected turbidity. The output signal of the turbidity sensor 14 is applied to the controller 13. When the rotational speed of the blood pump increases and reaches a rate ranging from 160 to 200 ml/min, platelets contained in the buffy coat layer that have stayed in the centrifugal separator 20 flow out therefrom. As a result of the release of the platelets, the turbidity of the liquid passing through the turbidity sensor 14 becomes high. At a time point when a voltage outputted from the turbidity sensor 14 drops by 0.2 V, the third flow path shutter means 83 is closed and the fourth flow path shutter means 84 is opened. Thus the platelet-rich plasma released from the centrifugal separator 20 is collected in the platelet collection bag 26. The controller 13 converts the voltage outputted from the turbidity sensor 14 into a platelet concentration to compute a platelet concentration in the platelet collection bag 26 during the platelet collection operation. The platelet concentration in the platelet collection bag 26 drops after reaching a maximum value. At a time point when it is detected that the maximum concentration has been attained, the execution of the platelet collection step finishes and the process proceeds to the buffy coat collection step.

Upon completion of the platelet collection step, the buffy coat collection step is executed. In this step, the controller 13 closes the fourth flow path shutter means 84 and opens the fifth flow path shutter means 85. The plasma in the plasma collection bag 25 is fed to the centrifugal separator 20 by the blood pump 11. At the same time, the liquid that has been released (the buffy coat layer that has flowed out) from the centrifugal separator 20 flows into the buffy coat collection bag 27. In the buffy coat collection step, the final rate of the rotational speed of the blood pump in the platelet collection step is maintained, and the rotational speed of the centrifugal separator 20 is decreased to 4600 rpm. In this manner, the buffy coat is released from the centrifugal separator 20 and collected in the buffy coat collection bag 27. At a time point when the amount of the collected buffy coat reaches a value computed based on the hematocrit value of the donor and the amount of collected platelet, the blood pump 11 is stopped and all the valves are closed. Thus the centrifugal separator 20 stops rotating, i.e., the execution of the buffy coat collection step terminates.

Then, the blood return step of returning the blood in the centrifugal separator 20 to the donor is executed. The controller 13 rotates the blood pump 11 in a reverse direction, opens the first flow path shutter means 81, and returns the red cell layer remaining in the centrifugal separator 20 to the donor through the first line 21.

Thus, the first (initial) platelet collection operation terminates.

Figure 13:
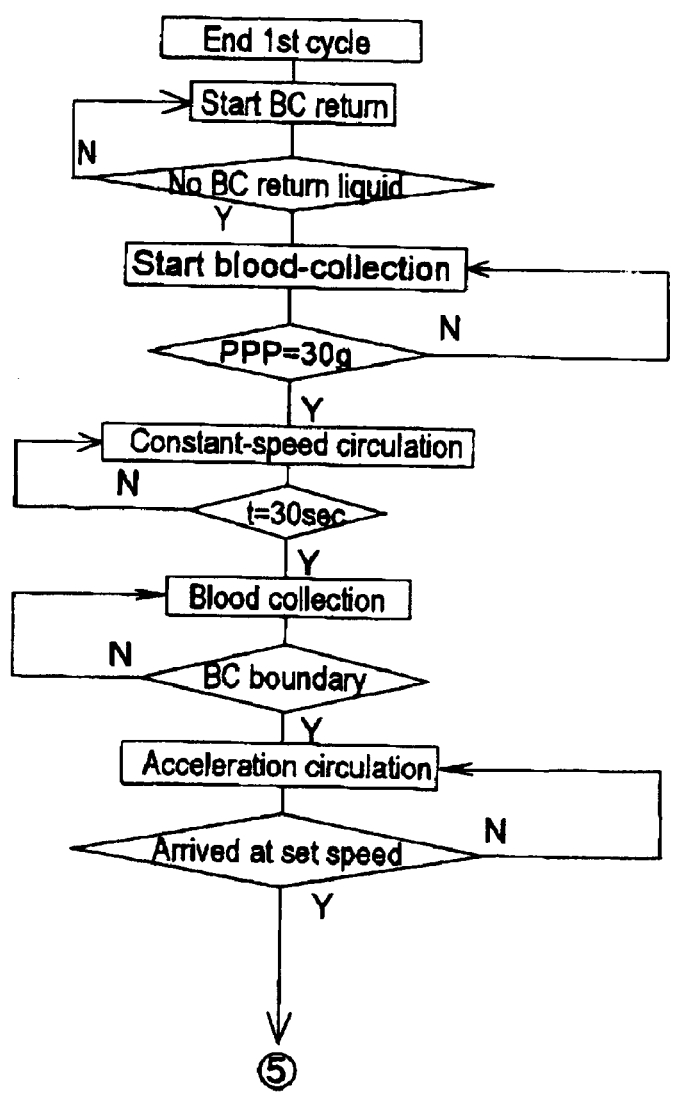
FIG. 13 is the flowchart for describing the operation of a blood component collection apparatus according to the present invention.

Then, the process proceeds to a second platelet collection operation, as shown in FIG. 13.

First, referring to FIG. 13, the controller 13 executes the buffy coat return step of returning the buffy coat collected in the first platelet collection step to the centrifugal separator 20 before the next blood collection step is executed. Once the process proceeds to the buffy coat return step, the controller 13 rotates the centrifugal separator 20 at a predetermined rotational speed (for example, 4800 rpm), opens the fifth flow path shutter means 85 and the fourth flow path shutter means 84, and starts the blood pump 11 at a predetermined rate (default value: 100 ml/min). The buffy coat contained in the buffy coat collection bag 27 is fed to the centrifugal separator 20 through the fifth flow path shutter means 85. The air in the centrifugal separator 20 is sent to the platelet collection bag 26 through the second line 22 and the fourth flow path shutter means 84. After the blood pump 11 rotates in an amount corresponding to the set collection amount of the buffy coat, the execution of the buffy coat return step is completed.

Figure 14:
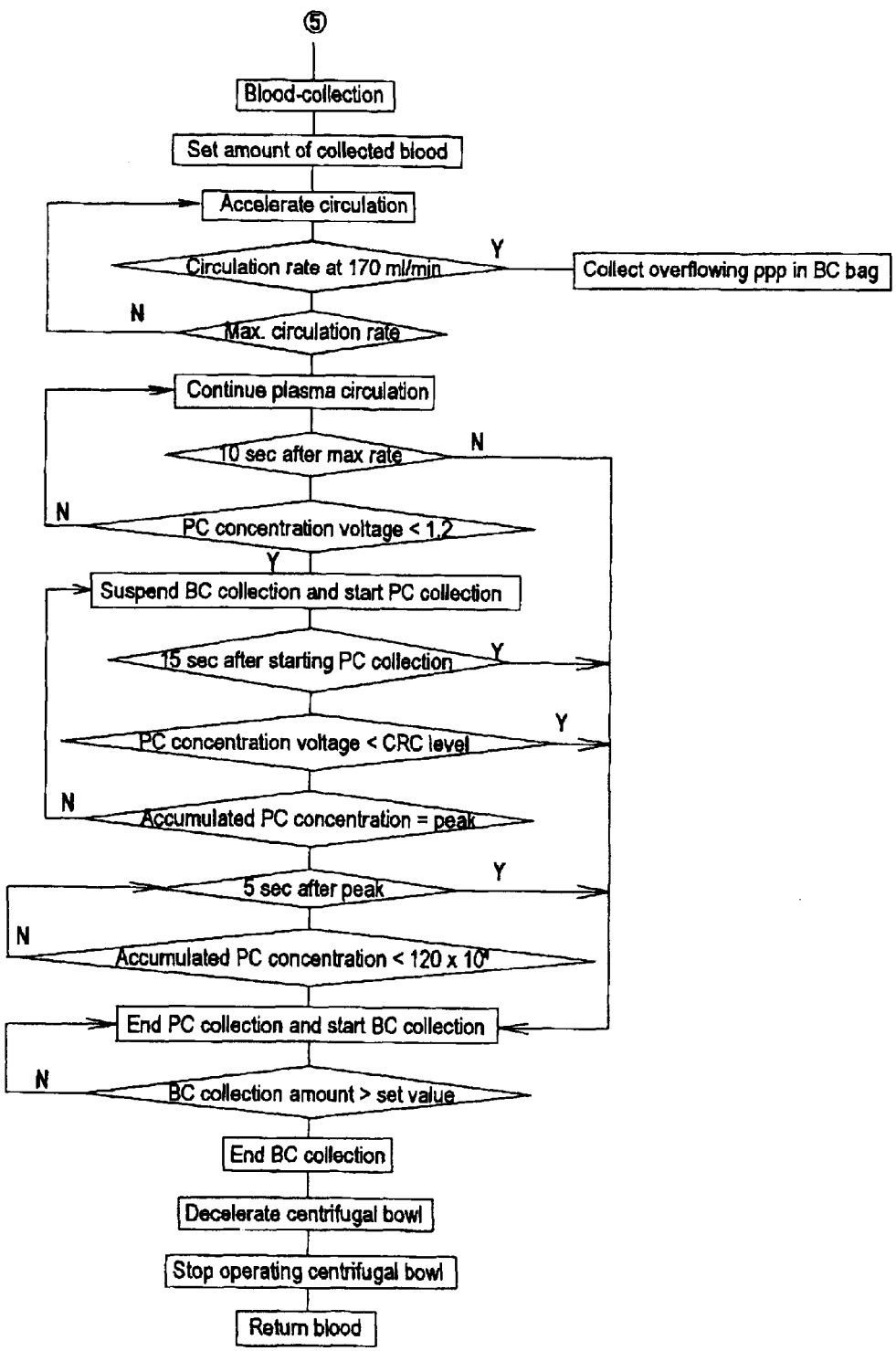
FIG. 14 is a flowchart for describing the operation of the blood component collection apparatus according to the present invention.

Then, the process proceeds to the program referred to as ⑤ shown in FIG. 14 after termination of the execution of the first plasma collection step, the constant-speed circulation step, the second plasma collection step, and the acceleration circulation step. Then, the controller 13 executes the blood collection step for boundary adjustment, the platelet collection step, the buffy coat collection step, and the blood return step to complete the second platelet collection operation.

Figure 15:
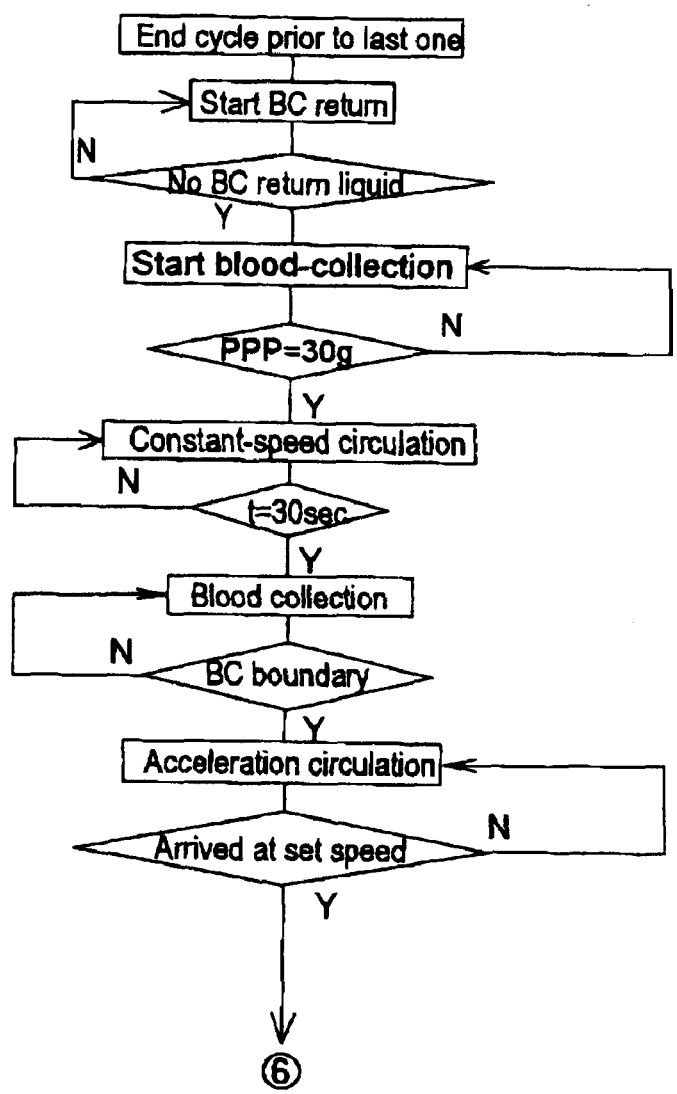
FIG. 15 is a flowchart for describing the operation of the blood component collection apparatus according to the present invention.

Now, explanation will be given on the last platelet collection operation as shown in FIG. 15. In this embodiment, the second operation is the last one. However, the third or subsequent platelet collection operation may be the last one as far as similar effects can be obtained. Each of these platelet collection operations except the last one is identical to the second platelet collection operation (FIGS. 13 and 14).

First, as shown in FIG. 15, the buffy coat return step is executed. In this step, the buffy coat collected by the second platelet collection operation is returned to the centrifugal separator 20 prior to the execution of the next blood collection step.

When the process proceeds to the buffy coat return step, the controller 13 rotates the centrifugal separator 20 at a predetermined rotational speed (for example, 4800 rpm), opens the fifth flow path shutter means 85 and the fourth flow path shutter means 84, and activates the blood pump 11 at a predetermined rate (default value: 100 ml/min). The buffy coat contained in the buffy coat collection bag 27 passes through the fifth flow path shutter means 85 and is supplied to the centrifugal separator 20. The air in the centrifugal separator 20 is sent to the platelet collection bag 26 through the second line 22 and the fourth flow path shutter means 84. After the blood pump 11 rotates in an amount corresponding to the set collection amount of the buffy coat, the execution of the buffy coat return step terminates.

Then, the first plasma collection step is executed. That is, the first and second liquid supply pumps 11, 12 are started to collect the anticoagulant-added blood, and the centrifugal separator drive unit 10 is activated to collect a first predetermined amount of plasma from the blood and flow it into the plasma collection bag 25.

Upon start of the first blood collection, the first liquid supply pump 11 is rotated at a predetermined rate (for example, 60 ml/min). At this time, the second pump constituting the anticoagulant pump supplies the anticoagulant (such as the ACD-A solution) at the predetermined rate (for example, 1/10 of the blood pump rate). Blood supplied from the donor is mixed with the ACD-A solution. The ACD-A solution-added blood flows through the first line 21, passes through the chamber and the first flow path shutter means 81, and flows into the centrifugal separator 20. At this time, the sixth flow path shutter means 86, the fifth flow path shutter means 85, the second flow path shutter means 82, the third flow path shutter means 83, and the seventh flow path shutter means 87 are closed. Meanwhile the first flow path shutter means 81 and the fifth flow path shutter means 85 are opened. When the ACD-A solution-added blood is supplied to the centrifugal separator 20, the sterilized air that has been admitted into the centrifugal separator 20 flows into the buffy coat collection bag 27 through a line sensor and the fifth flow path shutter means 85. Simultaneously with the start of the blood collection step, the centrifugal separator 20 starts rotating at the predetermined speed (for example, 4800 rpm). The centrifugal separator 20 is supplied with the ACD-A solution-added blood during its rotation. Thus, the centrifugal separator 20 separates it centrifugally into the plasma layer (inner layer), the buffy coat layer (BC layer, intermediate layer), and the red cell layer (outer layer). When about 270 ml of the ACD-A solution-added blood exceeding the capacity of the centrifugal separator is supplied to the centrifugal separator 20, it is filled with the blood, and the plasma overflows through the outlet of the centrifugal separator 20. The turbidity sensor 14 mounted on the second line 22 connected to the outlet of the centrifugal separator 20 detects that the fluid flowing through the line has changed from the air to the plasma. Based on the detection signal outputted from the turbidity sensor 14, the controller 13 closes the fifth flow path shutter means 85 and opens the third flow path shutter means 83 to collect the plasma into the plasma collection bag 25. The weight of the plasma collection bag 25 is measured in advance by the weight sensor 16, and a signal indicating the measured weight is transmitted therefrom to the controller 13. Thus, when the weight of the plasma collected in the plasma collection bag 25 is increased to a predetermined amount (for example, 30 g), the controller 13 closes the first flow path shutter means 81 and opens the second flow path shutter means 82 to proceed to the constant-speed plasma circulation step.

Figure 16:
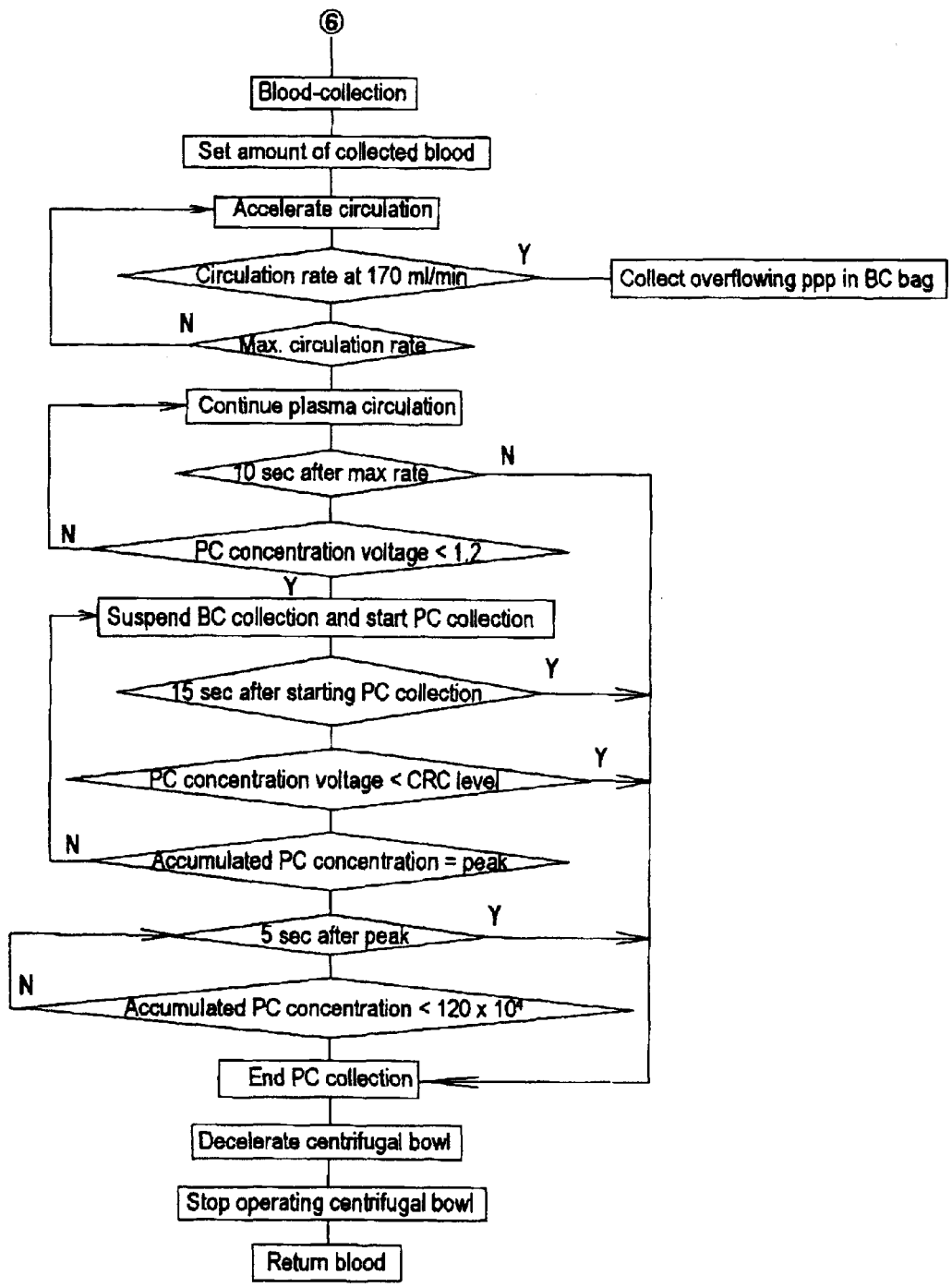
FIG. 16 is a flowchart for describing the operation of the blood component collection apparatus according to the present invention.

After the execution of the above-mentioned constant-speed circulation step, the second plasma circulation step, and the acceleration circulation step terminate, the process proceeds to the program referred to as ⑥ in FIG. 16 to execute the blood collection step for boundary adjustment, the platelet collection step, and the blood return step sequentially. Thereafter, the last platelet collection operation terminates. The last and second platelet collection operations are different from each other in that different air introduction bags are used in the constant-speed plasma circulation step of both operations and that the blood return step is executed without executing the buffy coat collection step in the last platelet collection operation.

It is known that in a particle suspension, as a particle concentration becomes higher, the apparent viscosity of the particle suspension becomes increasingly high. As the apparent viscosity becomes higher, the difference among sedimentation rates of particles having different specific gravities becomes increasingly high. When this fact is applied to the platelet collection step, it follows that as the apparent viscosity of the particle suspension in the centrifugal separator 20 becomes higher, the probability that the white cells having higher specific gravity than that of the platelets flow out together with the platelets becomes increasingly high. During the blood collection, the centrifugal separator 20 is rotating and a centrifugal force is constantly applied to the blood components in the centrifugal separate 20. Each blood component in the centrifugal separator 20, therefore, is progressively concentrated by the centrifugal force. Therefore, as shown in FIG. 3, the blood is separated into a red cell layer (outer layer), a buffy coat layer (intermediate layer), and a plasma layer (inner layer). The size of particles in each layer decreases sequentially in the direction from the outside of the centrifugal separator 20 to the inside thereof.

A plurality of what is called cake layers is formed in the centrifugal separator 20. The cake layers are gradually compressed. New whole blood flows into the centrifugal separator 20 from the cake layer formed of outermost blood cells and is trapped thereby. Meanwhile the other blood components pass through the cake layer and move to the buffy coat layer and the plasma layer. In the case where the blood cell cake layer and the buffy coat cake layer are excessively compressed, the gap between fine particles in each of the blood cell cake layer and the buffy coat cake layer is reduced. This leads to a phenomenon that platelets are trapped in the cell cake layer or the buffy coat cake layer. Thus, the collection efficiency of the platelets deteriorates.

According to the present invention, the plasma collection step is divided into a plurality of steps. Therefore, the time length of each plasma collection step can be shortened. Further, the cake layers are compressed very slowly by executing the acceleration plasma circulation step after the second blood collection terminates. In particular, because the acceleration plasma circulation step is executed, the cake layers are compressed very slowly and platelets embedded in a CRC layer (concentrated red cell layer) are moved upward even though the final circulation rate of plasma is set high. Thus, it is possible to collect the platelets into the BC layer. Because the BC layer is also moved upward, it is possible to accelerate separation and arrangement of the platelets and WBC (white cells) in the BC layer. Therefore, the platelets can be collected at improved collection efficiency.

EXAMPLES

An apparatus having a circuit, as shown in FIG. 4, including two pumps of an ACD pump 12 and a blood pump 11 was prepared to compare the platelet collection performance of the example and that of a comparison example. Comparison tests were conducted on the same donor at an interval of two weeks or longer. Evaluated operation flows were compared as shown below (n=2 examples). The number of obtained platelets contained in concentrated plasma and the number of white cells (WBC) were measured by Sysmex (R) NE-6000. The lower limit of the number of WBC which can be measured by the Sysmex NE-6000 was $0.1 \times 10^2$[cells/muL]. Thus, Nageotte [1:9] method was used to measure the number of white cells of the samples that were lower than the lower limit. The collected amount of platelet was 40 ml.

Platelet collection operation was performed twice, using the above-described method. Blood collection rate was 60 ml/min. After the total amount of plasma reached 30 g, a first circulation was conducted under a condition of 200 ml/min for 30 seconds. After a BC boundary was detected, a second circulation was conducted under a condition of an initial rate of 60 ml/min for 30 seconds, an arrival rate of 200 ml/min, an acceleration of 6.7 ml/min/sec, and an accelerated time period of 21 seconds. The acceleration condition at a platelet collection time was 2.2 ml/min/sec. The platelet collection rate was 200 ml/min until the concentration of platelet attained a predetermined one. The buffy coat collection rate was 205 ml/min, 40 ml. In the second platelet collection operation, buffy coat was not collected.

Comparison Example

The same apparatus as that used in the example was employed. The platelet collection operation was performed twice under the following conditions: The blood collection rate was 60 ml/min. After an optical sensor detected a buffy coat layer, a first circulation was conducted at the rate of 200 ml/min for 3 seconds, and a second circulation was conducted at the rate of 200 ml/min for 20 seconds. Platelets were collected at an acceleration rate of 8 ml/min/sec until the concentration of platelet attained 50 % of the maximum concentration.

The concentration of platelets contained in concentrated plasma and the concentration of white cells in the example and the comparison example are shown as follows:

TABLE 3

|  | Platelet concentration [cells/muL] | |
| --- | --- | --- |
|  | Sample 1 | Sample 2 |
| Example | $113.8 \times 10^4$ | $126.5 \times 10^4$ |
| Comparison Ex. | $104.4 \times 10^4$ | $112.4 \times 10^4$ |

TABLE 4

|  | White cell concentration [cells/muL] | |
| --- | --- | --- |
|  | Sample 1 | Sample 2 |
| Example | $0.1 \times 10^1$ | $0.1 \times 10^2$ |
| Comparison Ex. | $0.4 \times 10^2$ | $0.6 \times 10^2$ |

The blood component collection apparatus according to the present invention has two pumps. Thus, it can be reduced in size. A blood collection is temporarily suspended in a given platelet collection operation. The plasma re-circulation step for re-circulating collected plasma to the centrifugal separator is executed at least twice. Further, the plasma re-circulation step is executed as the acceleration circulation in a later time. Therefore, it is possible to prevent a blood cell layer and a buffy coat layer from being excessively compressed in the centrifugal separator, move upward platelets embedded in a concentrated red cell layer, and collect platelets into the buffy coat layer. Because the buffy coat layer also moves upward, it is possible to accelerate separation and arrangement of the platelets and white cells in the buffy coat layer. Therefore, the blood component collection apparatus produces a high-concentration platelet-containing solution (plasma containing concentrated platelets) that contains a small number of white cells at a high platelet collection efficiency.

What is claimed is:

1. A blood component collecting method using a blood component collecting circuit including a centrifugal separator having an internal blood storage space in which a rotor is disposed, an inlet and an outlet communicating with said blood storage space for centrifugally separating the blood introduced therein through said inlet by rotation of said rotor; a first line for connection between a blood source and said inlet of said centrifugal separator, a second line connected to said outlet of said centrifugal separator, a third line connected to said first line for injecting an anticoagulant, a plasma collecting bag having a first tube connected to an intermediate point of said first line and a second tube connected to said second line, and a platelet collecting bag connected to said second line, said method comprising the steps of:

A) collecting and circulating plasma by:
   A1) delivering from said source to said separator, blood to which anticoagulant has been added,
   A2) operating said rotor to separate plasma from the blood, and collecting the plasma in said plasma collecting bag, thereafter
   A3) terminating step A1, thereafter
   A4) circulating said plasma between said plasma collecting bag and said separator, and
   A5) repeating steps A1–A4 sequentially at least once to increase the amount of collected blood; thereafter B) collecting platelets by:
   B1) delivering to said separator additional blood to which anticoagulant has been added,
   B2) circulating the plasma between said plasma collecting bag and said separator at an accelerating circulation rate while rotating said rotor to remove platelets from said separator, and
   B3) collecting said platelets in said platelet collecting bag; and thereafter C) returning, to said source, a blood component remaining in said separator.

2. The method according to claim 1 wherein step A2 is performed until a predetermined amount of plasma has been collected in said plasma collecting bag, step A4 comprising circulating said plasma at a constant speed.

3. The method according to claim 1 wherein steps A, B and C are performed in sequence, at least two times.

4. The blood component collecting method according to claim 1 wherein step A4 is performed at a constant speed, and step A5 comprises repeating steps A1–A4 wherein repeated step A4 is performed at an accelerated speed.

* * * * *